(12) United States Patent
Rumbaugh et al.

(10) Patent No.: US 11,878,050 B2
(45) Date of Patent: Jan. 23, 2024

(54) GLYCOSIDE HYDROLASES TO TREAT BIOFILM-ASSOCIATED INFECTIONS

(71) Applicant: Texas Tech University System, Lubbock, TX (US)

(72) Inventors: Kendra Rumbaugh, Lubbock, TX (US); Derek Fleming, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 131 days.

(21) Appl. No.: 16/512,440

(22) Filed: Jul. 16, 2019

(65) Prior Publication Data

US 2020/0016245 A1    Jan. 16, 2020

Related U.S. Application Data

(60) Provisional application No. 62/698,346, filed on Jul. 16, 2018.

(51) Int. Cl.
| | | |
|---|---|---|
| A61K 38/47 | (2006.01) | |
| A61P 31/04 | (2006.01) | |
| A61K 31/407 | (2006.01) | |
| A61K 38/51 | (2006.01) | |
| A61K 9/00 | (2006.01) | |

(52) U.S. Cl.
CPC ............ *A61K 38/47* (2013.01); *A61K 9/0014* (2013.01); *A61K 31/407* (2013.01); *A61K 38/51* (2013.01); *A61P 31/04* (2018.01)

(58) Field of Classification Search
CPC ....... A61K 38/47; A61K 9/0014; A61P 31/04; A61L 2300/406; A61L 2300/254
See application file for complete search history.

(56) References Cited

U.S. PATENT DOCUMENTS

2002/0037260 A1    3/2002  Budny et al.
2007/0190152 A1*   8/2007  Bott ........................ A61K 47/24
                                                          424/486

FOREIGN PATENT DOCUMENTS

| WO | WO-0017331 | * | 3/2000 | ............... C12N 9/24 |
| WO | 2008070387 A1 | | 6/2008 | |
| WO | WO-2015184526 A1 | * | 12/2015 | ............... C12N 9/24 |
| WO | 2017197280 A1 | | 11/2017 | |

OTHER PUBLICATIONS

Ren et al. Efficient Eradication of Mature Pseudomonas aeruginosa Biofilm via Controlled Delivery of Nitric Oxide Combined with Antimicrobial Peptide and Antibiotics. Front. Microbiol. 2016;7:1-8.*
Fleming, Derek et al. "Glycoside Hydrolases Degrade Polymicrobial Bacterial Biofilms in Wounds" Antimicrobial Agents and Chemotherapy, Feb. 2017, vol. 61, Issue 2, 9 pages.

* cited by examiner

*Primary Examiner* — Lynn Y Fan

(74) *Attorney, Agent, or Firm* — Edwin S. Flores; Daniel J. Chalker; Chalker Flores, LLP

(57) ABSTRACT

The present invention includes methods for reducing biofilm present on a surface comprising contacting the surface with a composition under conditions wherein the presence of the biofilm on the surface is reduced and antibiotic activity is increased, wherein the composition comprises at least two glycoside hydrolases and an antibiotic.

8 Claims, 14 Drawing Sheets

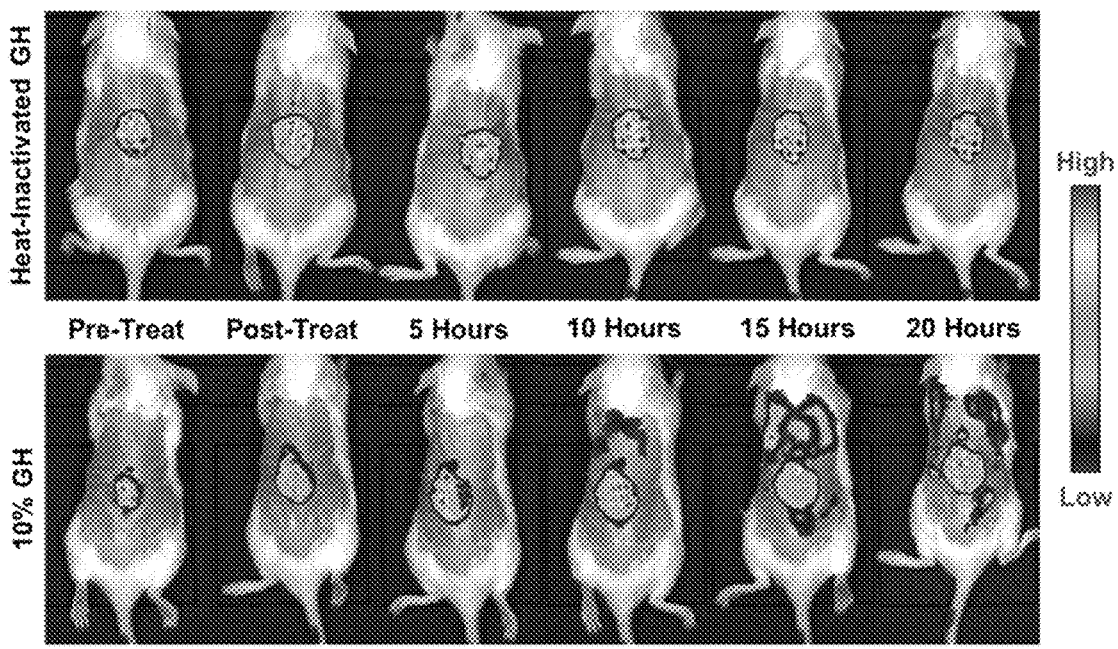
FIG. 11
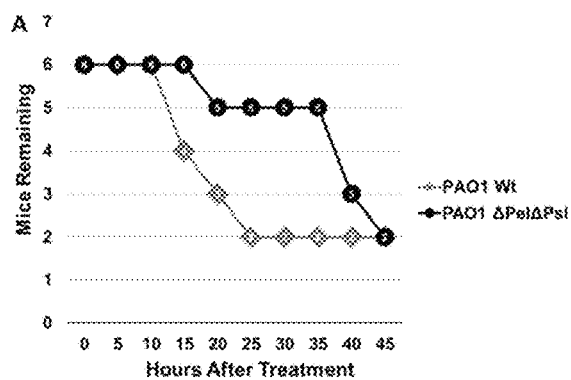
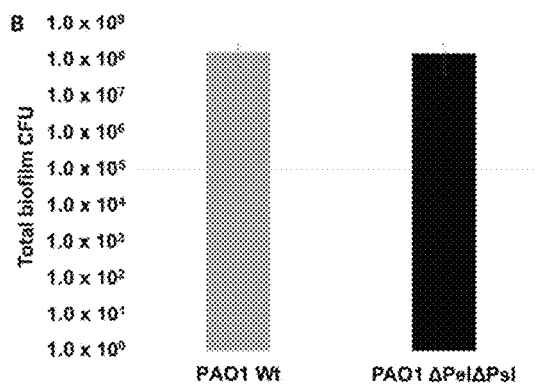
FIG. 12A  FIG. 12B (b)

GLYCOSIDE HYDROLASES TO TREAT BIOFILM-ASSOCIATED INFECTIONS

CROSS-REFERENCE TO RELATED APPLICATIONS

This application claims priority to U.S. Provisional Application Ser. No. 62/698,346, filed Jul. 16, 2018, the entire contents of which are incorporated herein by reference.

STATEMENT OF FEDERALLY FUNDED RESEARCH

This invention was made with government support under RZ1A1137462 awarded by the National Institute of Health. The government has certain rights in the invention.

TECHNICAL FIELD OF THE INVENTION

The present invention relates in general to the field of treating biofilms, and biofilm-associated infections.

BACKGROUND OF THE INVENTION

Without limiting the scope of the invention, its background is described in connection with biofilms in chronic infections.

Chronic infections are often exacerbated by the presence of a biofilm, a complex community of microorganisms living within a matrix of polysaccharides, proteins, eDNA, lipids and other molecules that comprise the extracellular polymeric substance (EPS). Living within the protection of the EPS, one or multiple species of microbes are afforded greatly increased tolerances to both antimicrobials and host defenses. Biofilm-associated tolerance is due to several proposed mechanisms. The EPS provides a physical barrier that can be difficult for antibiotics to penetrate, and bacteria within the biofilm often display reduced metabolic activity, which greatly influences their susceptibility to antibiotics, the majority of which depend on active metabolism. Thus, biofilm infections, which have been estimated to include 80% of all human bacterial infections, and 90% of chronic wound infections, are highly recalcitrant to traditional therapies.

As an alternative approach to directly targeting the causative pathogens of a biofilm infection, many researchers have directed their efforts towards degrading EPS matrix constituents. In theory, dispersal of biofilm microbes into their planktonic form will increase their susceptibility to antimicrobials and the host immune system. Further, because they do not directly target the microorganisms themselves, they should be less likely to drive resistance. To date, a host of EPS-specific dispersal agents have been investigated, with targets including, but not limited to, structural exopolysaccharides, exoproteins, and eDNA[3,6]. However, it should be noted that clinical application of such therapies are virtually non-existent, with the exception of Dornase alpha (Pulmozyme®) as an FDA-approved therapy for the breakup of DNA-rich mucus presenting in cystic fibrosis patients[8], but which also may be active on biofilms in the lungs. While medically induced dispersal of a mature biofilms in vivo has yet to be demonstrated, EPS-targeting, especially enzymatic-mediated deconstruction of matrix constituents, represents a promising antibiofilm avenue.

Exopolysaccharides are one of the major structural components for the majority of EPS producers. EPS producers play a variety of vital roles in biofilm formation and persistence, including but not limited to: surface and cell-cell adhesion and aggregation, tolerance to desiccation, mechanical stability, nutrient sorption and storage, binding of enzymes, and physical protection against antimicrobials and the environment. Considering their ubiquity and importance to the structural integrity of the EPS matrix, active degradation of exopolysaccharides represents a promising approach to clinically eradicating biofilm infections.

Previous work by the present inventors showed that a dual-enzyme combination of α-amylase and cellulase resulted in significant reductions in biomass, and the dispersal of biofilm-dwelling bacteria, allowing for an increase in the effectiveness of antibiotic treatments in vitro Fleming, D., Chahin, L. & Rumbaugh, K. Glycoside Hydrolases Degrade Polymicrobial Bacterial Biofilms in Wounds. *Antimicrob Agents Chemother* 61, doi:10.1128/AAC.01998-16 (2017). However, it has been hypothesized and commonly understood that triggering a large-scale dispersal event in a living host can overwhelm the immune system, causing dissemination of the infection and possibly lethal septicemia[15].

Thus, a need remains for compositions and methods for the elimination of biofilms, the treatment of chronic wounds, and methods for treating a wide variety of wounds that fester as a result of microbially formed-biofilms.

SUMMARY OF THE INVENTION

In one embodiment, the present invention includes a method for reducing biofilm present on a surface, wherein the method comprises contacting the surface with a composition under conditions wherein the presence of the biofilm on the surface is reduced and antibiotic activity is increased, wherein the composition comprises at least two glycoside hydrolases and an antibiotic. In one aspect, the biofilm comprises one or more pathogenic bacteria. In another aspect, the two or more glycoside hydrolases are a bacterial alpha-amylase and a fungal cellulase. In another aspect, the two or more glycoside hydrolases are a bacterial alpha-amylase and a fungal cellulose at a 1:2, 1:1, or 2:1 ratio. In another aspect, the two or more glycoside hydrolases are at least 1, 2, 3, 4, 5, 7, 10, 12, 15, 20, 25, 30, 35, 40, 45, 50, 60, 70, 80, or 90% weight to weight of the composition. In another aspect, the method further comprises co-administering topically, systemically, or both an antimicrobial agent to an animal in need thereof. In another aspect, the two glycoside hydrolases increase the effectiveness of the antibiotic at least 10, 20, 25, 30, 35, 40, 45, 50, 75, 100, 200, 300, 400, 500, 600, 700, 800, 900, or 1000%, when compared to a biofilm that is not exposed to the at least two glycoside hydrolases. In another aspect, the surface is a surface of a catheter. In another aspect, a biofilm-related infection is the result of a wound, burn infection, keratitis, bioprosthetic or indwelling medical device infection in the animal or wherein the biofilm-related infection is in the lung of the animal and wherein the animal has chronic pulmonary disease or lung infection. In another aspect, the biofilm of a biofilm-related infection is *P. aeruginosa, S. aureus, E. coli, Aeromonas* spp., *Enterobacteriaceae* spp., *Candida* spp., *Aspergillus* spp., *Acinetobacter* spp., *T. asahii, B. cineria* and/or *Fusarium* spp. In another aspect, the subject is selected from the group consisting of a subject coincidentally also suffering from a condition selected from the group consisting of human immunodeficiency virus (HIV), sepsis, septic shock, acquired immunodeficiency syndrome (AIDS), leukemia, a lymphoma, rheumatoid arthritis, diabetes mellitus type I, Crohn's disease, chronic obstructive pulmonary disease (COPD), bronchitis, cystic fibrosis, emphysema, lung carcinoma, asthma, pneumonia and sinusitis, a subject preparing for, undergoing, or recovering from chemotherapy, radiotherapy, or an organ transplant, a resident in a healthcare institution and a smoker. In another aspect, the method further comprises treating dental plaque, gingivitis, periodontitis, native valve endocarditis, acute otitis media, chronic bacterial prostatitis, pneumonia, asthma or device-related infection resulting from implantable and/or prosthetic medical devices or tissue replacements. In another aspect, the biofilm is in or on an internal or external body surface or interface selected from the group consisting of a surface in an oral cavity, a reproductive tract, a urinary tract, a respiratory tract, a gastrointestinal tract, a peritoneum, a middle ear or a prostate; vascular intima; conjunctiva; corneal tissue; lung tissue; heart valves; skin; scalp; nails; teeth and an interior of a wound. In another aspect, the subject is selected from the group consisting of a subject coincidentally also suffering from a different pre-established infection, an immunocompromised subject, a subject also undergoing intensive or critical care, a subject also suffering from trauma, a subject also suffering from a burn, a subject also suffering from an acute and/or chronic wound, a neonatal subject, an elderly subject, a subject also suffering from a malignant neoplasm, a subject also suffering from a non-malignant neoplasm, a subject also suffering from an auto-immune condition, a subject also suffering from reduced or abrogated epithelial or endothelial secretion and/or secretion clearance and a subject also fitted with a medical device. In another aspect, the surface is exposed skin, or an internal surface of the mammal. In another aspect, the two or more glycoside hydrolases are selected from α-amylase, diastase, pectolyase, pectinase, invertase, amylogulcosidase, dextranase, cellulose, xylanase, alginate lyase, cytohelicase, and inulinase. In another aspect, the surface is a non-medical surface that is susceptible to biofilm formation. In another aspect, the biofilm is Pel-dependent, Psl-dependent, PNAG-dependent, GAG-dependent biofilm, and wherein the biofilm is caused by at least one of: *P. aeruginosa, S. aureus, E. coli, S. epidermidis, Y. pestis, B. pertussis, Burkholderia* spp., *Candida* spp., *Aspergillus* spp., *Acinetobacter* spp., or *Fusarium* spp.

In another embodiment, the present invention includes a method of inhibiting a biofilm infection in a mammal, the method comprising: identifying the presence of the biofilm infection, and administering to the mammal a therapeutically effective amount of a composition comprising at least two glycoside hydrolases and an antibiotic in amounts capable of significant biofilm degradation in the mammal, in an amount and for a time sufficient to cause significant biofilm degradation within the mammal, and that does not cause septicemia in the mammal. In one aspect, the biofilm comprises one or more pathogenic bacteria. In another aspect, the two or more glycoside hydrolases are a bacterial alpha-amylase and a fungal cellulase. In another aspect, the two or more glycoside hydrolases are a bacterial alpha-amylase and a fungal cellulose at a 1:2, 1:1, or 2:1 ratio. In another aspect, the two or more glycoside hydrolases are at least 1, 2, 3, 4, 5, 7, 10, 12, 15, 20, 25, 30, 35, 40, 45, 50, 60, 70, 80, or 90% weight to weight of the composition. In another aspect, the method further comprises co-administering topically, systemically, or both an antimicrobial agent to an animal in need thereof. In another aspect, the surface is a surface of a catheter. In another aspect, a biofilm-related infection is the result of a wound, burn infection, keratitis, bioprosthetic or indwelling medical device infection in the animal or wherein the biofilm-related infection is in the lung of the animal and wherein the animal has chronic pulmonary disease or lung infection. In another aspect, the biofilm of a biofilm-related infection is *P. aeruginosa, S. aureus, E. coli, Aeromonas* spp., *Enterobacteriaceae* spp., *Candida* spp., *Aspergillus* spp., *Acinetobacter* spp., *T. asahii, B. cineria* and/or *Fusarium* spp. In another aspect, the subject is selected from the group consisting of a subject coincidentally also suffering from a condition selected from the group consisting of human immunodeficiency virus (HIV), sepsis, septic shock, acquired immunodeficiency syndrome (AIDS), leukemia, a lymphoma, rheumatoid arthritis, diabetes mellitus type I, Crohn's disease, chronic obstructive pulmonary disease (COPD), bronchitis, cystic fibrosis, emphysema, lung carcinoma, asthma, pneumonia and sinusitis, a subject preparing for, undergoing, or recovering from chemotherapy, radiotherapy, or an organ transplant, a resident in a healthcare institution and a smoker. In another aspect, the method is for treating dental plaque, gingivitis, periodontitis, native valve endocarditis, acute otitis media, chronic bacterial prostatitis, pneumonia, asthma or device-related infection resulting from implantable and/or prosthetic medical devices or tissue replacements. In another aspect, the biofilm is in or on an internal or external body surface or interface selected from the group consisting of a surface in an oral cavity, a reproductive tract, a urinary tract, a respiratory tract, a gastrointestinal tract, a peritoneum, a middle ear or a prostate; vascular intima; conjunctiva; corneal tissue; lung tissue; heart valves; skin; scalp; nails; teeth and an interior of a wound. In another aspect, the subject is selected from the group consisting of a subject coincidentally also suffering from a different pre-established infection, an immunocompromised subject, a subject also undergoing intensive or critical care, a subject also suffering from trauma, a subject also suffering from a burn, a subject also suffering from an acute and/or chronic wound, a neonatal subject, an elderly subject, a subject also suffering from a malignant neoplasm, a subject also suffering from a non-malignant neoplasm, a subject also suffering from an auto-immune condition, a subject also suffering from reduced or abrogated epithelial or endothelial secretion and/or secretion clearance and a subject also fitted with a medical device. In another aspect, the surface is exposed skin, or an internal surface of the mammal. In another aspect, the two or more glycoside hydrolases are selected from α-amylase, diastase, pectolyase, pectinase, invertase, amylogulcosidase, dextranase, cellulose, xylanase, alginate lyase, cytohelicase, and inulinase. In another aspect, the biofilm is Pel-dependent, Psl-dependent, PNAG-dependent, GAG-dependent biofilm, and wherein the biofilm is caused by at least one of: *P. aeruginosa, S. aureus, E. coli, S. epidermidis, Y. pestis, B. pertussis, Burkholderia* spp., *Candida* spp., *Aspergillus* spp., *Acinetobacter* spp., or *Fusarium* spp. In another aspect, the method further comprises the step of pre-treating the mammal with systemic antibiotics. In another aspect, the method further comprises the step of determining the glycosidic linkages in an extracellular polymeric substance, and selecting the two or more glycosidic hydrolases in the composition. In another aspect, the method further comprises the step of measuring sepsis in the mammal and preventing the sepsis by providing antibiotics prophylactically, providing antibiotics concurrently, or both to the mammal.

BRIEF DESCRIPTION OF THE DRAWINGS

For a more complete understanding of the features and advantages of the present invention, reference is now made to the detailed description of the invention along with the accompanying figures and in which:

(FIG. 3B) 1.0% α-amylase significantly degraded pre-formed S. aureus and P. aeruginosa biofilms at all tested treatment times (2-60 minutes). One-way ANOVA and the Tukey-Kramer multiple-comparison test were used to test for differences between columns: $p<.01$, *$p<.001$.

(FIG. 7A) Percent biomass degraded was calculated as follows: (post-treatment weight/pre-treatment weight). (FIG. 7B) Percent dispersal was calculated as follows: (CFU in supernatant)/(CFU in supernatant+CFU remaining wound tissue-associated). One-way ANOVA and the Tukey-Kramer multiple-comparison test were used to test for differences between columns: *$p<0.001$, $p<0.01$.

(FIG. 8A) 1 hour treatment with 10% cellulase (shown) and α-amylase completely disassociates 24-hour-old polymicrobial biofilms (S. aureus+P. aeruginosa) cultured in wound-like media. (FIG. 8B) Treatment of 'wound-like biofilms' with 5% α-amylase+5% cellulase+200 μg/mL gentamicin sulfate was more effective at killing S. aureus and P. aeruginosa than gentamicin alone. One-way ANOVA and the Tukey-Kramer multiple-comparison test were used to test for differences between columns: *$p<0.001$, $p<0.01$.

FIG. 11 shows IVIS imaging of in vivo dispersal triggered by glycoside hydrolase therapy. Treatment of 48-hour-old mouse chronic wounds, infected with bioluminescent P. aeruginosa, with 10% α-amylase and cellulase (1:1; GH), or heat-inactivated control, resulted in dispersal and systemic spread of the infection. Clear localization of bacteria in the organs can be seen in the treated group. A representative animal from the treatment and control groups are shown.

FIGS. 12A and 12B are graphs that show that a double polysaccharide P. aeruginosa knockout mutant exhibits slower dispersal-mediated septicemia rates than the wild type. Treatment of 48-hour mouse chronic wounds, infected with either wild-type P. aeruginosa or a double polysaccharide knockout mutant (ΔPelΔPsl), with 10% α-amylase and cellulase (1:1; GH resulted in slower dispersal-mediated septicemia rates for the mutant (FIG. 12A). There was no significant difference between average wound bed bacterial loads for the two strains, indicating that bacterial numbers did not play a factor (FIG. 12B).

(FIG. 20A) Schematic illustration of the composition and structure of a multilayered film for releasing of Vancomycin. (FIG. 20B) Vancomycin loaded multilayered film (polyacrylic acid/PBAE/Vancomycin, 20 layers) was coated onto a wound dressing (Tegaderm). The film can be degraded by hydrolyzation, as shown in SEM and florescent images. Polyacrylic acid was labeled with FITC. Scale bar is 100 µm. (FIG. 20C) Release profile of Vancomycin can be adjusted by changing the film composition.

DETAILED DESCRIPTION OF THE INVENTION

Figure 1:
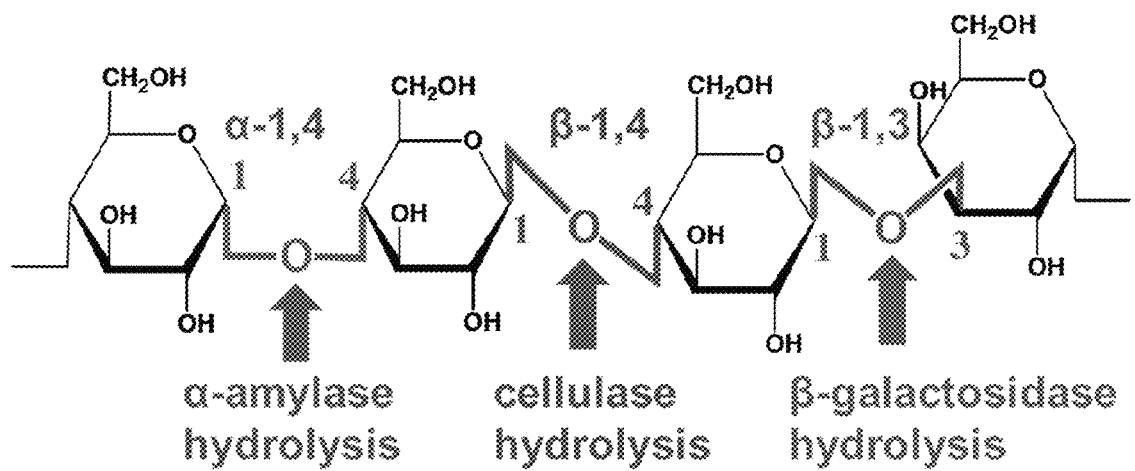
FIG. 1 shows examples of various glycosidic linkages found within the exopolysaccharides of biofilm EPS, and the enzymes that hydrolyze them.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

To target biofilm exopolysaccharides, the present inventors employed glycoside hydrolases (GHs), which are enzymes that hydrolyze the glycosidic linkages between two or more carbohydrates. They can be individually characterized by the specific type of linkage that they cleave, such as α-1,4 bond hydrolysis by α-amylase, β-1,4 bond hydrolysis by cellulase, or β-1,3 bond hydrolysis by β-1,3 galactosidase[1,12]. By targeting common, highly conserved glycosidic linkages, a single therapy can potentially prove efficacious against the EPS produced by a broad-spectrum of pathogens, and against the highly complex and compositionally chimeric polymicrobial biofilms often seen clinically[13]. Additionally, GHs are unlikely to pose significant risk to patients, because their targets (glycosidic linkages) are not readily found in human tissue.

As used herein, the terms "exopolysaccharide" or "extracellular Polymeric Substance" are often times used interchangeable, to refer to biofilm structural components that are vital to the overall mechanical stability of biofilms, in which polysaccharides play a host of other roles for biofilm initiation and persistence, including but not limited to: surface and scaffolding adhesion, microbial aggregation, desiccation tolerance, nutrient sorption and storage, enzyme binding, and physical protection against antimicrobials and host defenses. Considering their pervasiveness and utility, polysaccharides are a common target for anti-biofilm researchers, and glycoside hydrolases are at the forefront of prospective biofilm dispersal strategies. For example, Dispersin B, a glycoside hydrolase specific for the polysaccharide poly-N-acetylglucosamine (PNAG), has been shown to degrade the EPS of both Gram-positive and Gram-negative pathogens that contain the polysaccharide, and are currently being pursued for use in wound, oral, and lung infections in combination with DNAse I.

As used herein, the term "glycoside hydrolases", refers to a combination of two or more glycoside hydrolases that hydrolyze at least two different glycosidic linkages. Most commonly, the two different glycosidic linkages are cleaved concurrently. Non-limiting examples of glycosidic linkages for targeting by the two or more glycosidic hydrolases of the present invention include α-1-4, β-1,4, and β-1,3 glycosidic linkages. As taught herein, α-amylase and cellulase each target a separate, conserved, glycosidic linkage, and are able to degrade polymicrobial biofilms and increase antibiotic effectiveness. Such multi-glycoside hydrolase combinations, especially when coupled with additional classes of enzymes that target other conserved structural components, greatly bolster broad-spectrum applicability and clinical effectiveness.

Due to their importance for the establishment and maintenance of biofilm architecture, a significant amount of research into targeting exopolysaccharides with glycoside hydrolases as a means for dispersing biofilms has been performed. Table 1 lists many of the glycoside hydrolases that have biofilm-disrupting ability for use with the present invention.

TABLE 1

Glycoside Hydrolases that Disperse Biofilms

| Enzyme | Summary | References |
| --- | --- | --- |
| Alginate lyase | A glycoside hydrolase that that degrades the exopolysaccharide, alginate, common in mucoid *P. aeruginosa* biofilms, causing bacterial cell dispersal and increasing antibiotic efficacy and phagocytosis. | Lamppa J W, Griswold K E. Alginate lyase exhibits catalysis-independent biofilm dispersion and antibiotic synergy. Antimicrob Agents Chemother. 2013; 57(1): 137-45. Epub 2012 Oct. 17 |
| α-amylase | A glycoside hydrolase that hydrolyzes α(1,4) glycosidic linkages and is derived from multiple sources, such as certain microbes and the mammalian pancreas. It has exhibited dispersal of mature biofilms formed by *V. cholerae*, *S. aureus* and *P. aeruginosa*. | Fleming D, Chahin L, Rumbaugh K. Glycoside Hydrolases Degrade Polymicrobial Bacterial Biofilms in Wounds. Antimicrob Agents Chemother. 2017; 61(2). Epub 2016 Nov. 23. |
| α-mannosidase | An acid hydrolase that has been shown to disrupt *P. aeruginosa* biofilms. | Banar M, Emaneini M, Satarzadeh M, Abdellahi N, Beigverdi R, Leeuwen W B, et al. Evaluation of Mannosidase and Trypsin Enzymes Effects on Biofilm Production of *Pseudomonas aeruginosa* Isolated from Burn Wound Infections. PLoS One. 2016; 11(10): e0164622. Epub 2016 Oct. 14. |
| β-mannosidase | A glycoside hydrolase that targets β(1,4)-linked terminal mannose residues, and disrupts *P. aeruginosa* biofilms. | Banar M, Emaneini M, Satarzadeh M, Abdellahi N, Beigverdi R, Leeuwen W B, et al. Evaluation of Mannosidase and Trypsin Enzymes Effects on Biofilm Production of *Pseudomonas aeruginosa* Isolated from Burn Wound Infections. PLoS One. 2016; 11(10): e0164622. Epub 2016 Oct. 14. |
| Cellulase | A glycoside hydrolase produced by multiple microbes that hydrolyzes the β(1,4) glycosidic linkage. It has been shown to cause the dispersal of *S. aureus* and *P. aeruginosa* biofilms. | Fleming D, Chahin L, Rumbaugh K. Glycoside Hydrolases Degrade Polymicrobial Bacterial Biofilms in Wounds. Antimicrob Agents Chemother. 2017; 61(2). Epub 2016 Nov. 23. |
| Dispersin B | A glycoside hydrolase produced by the bacterium, *A. actinomycetemcomitans*, that has been shown to degrade the polysaccharide, poly (1,6)-N-acetyl-d-glucosamine (PNAG), by hydrolyzing β(1,6) glycosidic linkages. This enzyme has been effective against the biofilms made by multiple bacteria, including *S. aureus*, *A. actinomycetemcomitans*, *S. epidermidis*, *A. baumannii*, *K. pneumoniae*, *E. coli*, *Burkholderia* spp., *A. pleuropneumoniae*, *Yersinia pestis* and *Pseudomonas fluorescens*. | Waryah C B, Wells K, Ulluwishewa D, Chen-Tan N, Gogoi-Tiwari J, Ravensdale J, et al. In Vitro Antimicrobial Efficacy of Tobramycin Against *Staphylococcus aureus* Biofilms in Combination With or Without DNase I and/or Dispersin B: A Preliminary Investigation. Microb Drug Resist. 2016. Epub 2016 Oct. 19. |
| Hyaluronidase | An enzyme that cleaves hyaluronic acid (HA), which has been found to be incorporated into the biofilms made by multiple pathogens, including *S. aureus*, and *S. intermedius* in vivo. When utilized against HA-containing biofilms, dispersal has been observed. | Ibberson C B, Parlet C P, Kwiecinski J, Crosby H A, Meyerholz D K, Horswill A R. Hyaluronan Modulation Impacts *Staphylococcus aureus* Biofilm Infection. Infect Immun. 2016; 84(6): 1917-29. Epub 2016 Apr. 14. |
| PelAh | A glycoside hydrolase that disrupts the *P. aeruginosa* polysaccharide, Pel, causing dispersal of mature biofilms. | Baker P, Hill P J, Snarr B D, Alnabelseya N, Pestrak M J, Lee M J, et al. Exopolysaccharide biosynthetic glycoside hydrolases can be utilized to disrupt and prevent *Pseudomonas aeruginosa* biofilms. Sci Adv. 2016; 2(5): e1501632. Epub 2016 Jul. 08. |

TABLE 1-continued

Glycoside Hydrolases that Disperse Biofilms

| Enzyme | Summary | References |
| --- | --- | --- |
| PslGH | A glycoside hydrolase that disrupts the *P. aeruginosa* polysaccharide, Psl, causing dispersal of mature biofilms. | Baker P, Hill P J, Snarr B D, Alnabelseya N, Pestrak M J, Lee M J, et al. Exopolysaccharide biosynthetic glycoside hydrolases can be utilized to disrupt and prevent *Pseudomonas aeruginosa* biofilms. Sci Adv. 2016; 2(5): e1501632. Epub 2016 Jul. 08. |

As used herein, the term "chronic wound", refers to those wounds in which the normal healing process has been disrupted because, e.g., the wound has stalled in one of the healing stages. A chronic wound is a wound that has not healed within at least 40 days, at least 50 days, at least 60 days, at least 70 days, or at least 3, 6, 9, or 12 months.

As used herein, the term "antibiotic" refers to an antibacterial agents that include, but are not limited to, aminoglycosides (e.g., amikacin, gentamicin, kanamycin, neomycin, netilmicin, streptomycin, tobramycin); carbecephems (e.g., loracarbef); cephalosporins (eg cefadroxil, cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime); macrolides (e.g., azithromycin, clarithromycin, dirithromycin, erythromycin, roleandomycin); monobactams (e.g., aztreonam); penicillins (e.g. amoxicillin, ampicillin, carbenicillin, cloxacillin, dicloxacillin, nafcillin, oxacillin, penicillin G, penicillin V, piperacillin, ticarcillin); polypeptide antibiotics (e.g., bacitracin, colistin, polymyxin B); quinolones (e.g., ciprofloxacin, enoxacin, gatifloxacin, levofloxacin, lomefloxacin, moxifloxacin, norfloxacin, ofloxacin, trovafloxacin); sulfonamides (e.g., mafenide, sulfacetamide, sulfamethizole, sulfasalazine, sulfisoxazole, trimethoprim-sulfamethoxazole); tetracyclines (e.g., demeclocycline, doxycycline, minocycline, oxytetracycline, tetracycline); carbapenems (e.g., imipenem, meropenem, ertapenem, doripenem, panipenem/betamipron, biapenem, PZ-601); chloramphenicol; clindamycin, ethambutol; fosfomycin; isoniazid; linezolid; metronidazole; nitrofurantoin; pyrazinamide; quinupristin/dalfopristin; rifampin; spectinomycin; and/or vancomycin. In certain non-limiting examples, antibiotics such as vancomycin, tobramycin, meropenem, ciprofloxacin, piperacillin, colistin, aztreonam, ciprofloxacin and azithromycin are commonly used with the present invention.

As used herein, the term "antifungals" refers to antifungal agents that include, but are not limited to, polyenes (e.g., natamycin, rimocidin, filipin, nystatin, amphotericin B, candicin; imidazoles (e.g., miconazole, ketoconazole, clotrimazole, econazole, bifonazole, butoconazole, fenticonazole, isoconazole, oxiconazole, sertaconazole, sulconazole, tioconazole); triazoles (e.g., fluconazole, itraconazole, isavuconazole, ravuconazole, posaconazole, voriconazole, terconazole); allylamines (e.g., terbinafine, amorolfine, naftifine, butenafine); and/or echinocandins (e.g. anidulafungin, caspofungin, micafungin).

The composition of the present invention may conveniently be applied before, simultaneously with, or following a local or systemic antibiotic treatments. Conveniently, the local or systemic antibiotic treatment may be applied at substantially at the same time as the composition or afterwards. For example, the anti-microbial agent may be applied at least 1 hour, at least 3 hours, at least 5 and at least 6 hours after the composition is administered. In certain aspects, it has been found that to optimize the anti-microbial effect of the anti-microbial agent it can be administered or delivered repeatedly at time points appropriate for the agent used. The skilled person can devise a suitable dosage or usage regimen. In long-term treatments the composition can be used repeatedly. The frequency required will depend on the location of the biofilm infection, colony composition and the anti-microbial used and the skilled person is able to optimize the dosage or usage patterns to optimize results.

The composition of the present invention will often be used in combination with one or more mechanical and/or physical treatment of the site in need of elimination of biofilms and/or the one or more species of microbes that are forming the biofilm. For example, the anti-microbial agent may be used or applied after physical removal or reduction (debridement) of the biofilm from the surface. Following debridement of the biofilm, the surface may be contacted with the composition of the present invention for between 0 and 24 hours, 2 and 12 hours, 4 and 8 hours, 5 and 7 hours, or at least 6, 12, 18 or 24 hours. Following this initial time, an anti-microbial agent may be provided locally or systemically. As shown herein, the timing of the treatment can make a difference to reduce or eliminate the systemic effects of bacterial infections, such as sepsis, that is desirable in a clinical setting. In the case of biofilm infected wounds, such as chronic wounds, the duration of incubation may correspond to scheduled changes to the wound dressing. In fact, the composition may be part of the wound dressing.

The skilled artisan will recognize that physical removal of the biofilm may be carried out with any suitable surgical, mechanical or chemical treatment. Often, the surgical, mechanical or chemical treatment can also include the use of a liquid, gel, gel-sol, semi-solid compositions or gas applied at pressure to the biofilm, sonication, laser, or abrasive, preceded and/or followed by one or more wash steps using typical washing solutions, such as water, saline, etc., that may further include detergents, surfactants, salts, buffers, antimicrobial agents, etc. The debridement or wash solution it typically a sterile solution.

The composition of the present invention may be incorporated in one or more conventional carriers, diluents and/or excipients, to produce conventional preparations such as powders (e.g., inhalable powders), elixirs, suspensions, emulsions, solutions, syrups, aerosols (as a solid or in a liquid medium), sprays (e.g., nasal sprays), nebulizers, suppositories, sterile injectable solutions, topical solutions or gels, sterile packaged powders, and the like.

Non-limiting examples of suitable carriers, excipients, and diluents include, e.g., lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, lubricating agents, wetting agents, emulsifying agents, suspending agents, preserving agents, and the like.

For intravenous administration, the composition will be formulated into a sterile form that in a physiologically acceptable solution. Typical solutions are isotonic or slightly hypertonic, e.g., saline. Suitable liquids used for administering parenteral solutions include sodium chloride injection, ringers injection, dextrose injection, dextrose and sodium chloride injection, lactated ringers injection and other solutions described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000, and updates thereto; Martindale, The Extra Pharmacopoeia, Thirty-Second Edition (The Pharmaceutical Press, London, 1999); all of which are incorporated by reference, and the like, relevant portions incorporated herein by reference. The solutions can contain additional preservatives, buffers and antioxidants conventionally used for parenteral solutions, excipients and other additives which are compatible with the glycosidic hydrolases and which will not interfere with the manufacture, storage or use of products.

For topical administration, the composition can be incorporated into creams, ointments, gels, transdermal patches and the like. The composition can also be incorporated into medical dressings, for example wound dressings may be woven dressings or non-woven dressings (e.g., gels, hydrogels, polymeric matrices, thixotropic agents, etc.).

Example 1. Glycoside Hydrolases Degrade Polymicrobial Bacterial Biofilms in Wounds Chronic wound bacterial biofilm infections. Chronic wound bacterial biofilm infections (CWIs), which include pressure, diabetic, venous, and arterial ulcers, are a major clinical and economic burden worldwide. In fact, chronically-infected diabetic foot ulcers are considered the most significant wound care problem in the world [1]. Between 5 and 7 million Americans are treated for chronic wounds annually, at an estimated cost of 10-20 billion dollars per year; an expense which is expected to increase as the prevalence of risk factors, such as obesity and diabetes, grows [2]. CWIs largely owe their chronicity to the inability of the host to clear a biofilm, with or without clinical intervention. Biofilms are communities of microorganisms protected by a self-synthesized layer of complex polymers represented mainly by polysaccharides, proteins and eDNA, also called the extracellular polymeric substance (EPS). They form when a primary, planktonic bacterium irreversibly attaches itself to a surface and commences rapid division and recruitment of other microorganisms by providing more diverse adhesion sites to the substrate [3]. Under the protection of the EPS, such polymicrobial infections thrive, making wound healing difficult.

Several mechanisms have been proposed to explain how biofilms can contribute to the chronicity of wounds, including acting as a mechanical barrier against both host-derived and exogenous antimicrobial agents, as well as impeding the re-epithelialization process. This leads to a perpetual state of inflammation that delays wound healing [4, 5]. It is estimated that more than 90% of all chronic wounds contain bacteria that are biofilm-associated [6], making them up to 1,000-fold more tolerant to antibiotics and the host immune response [7]. Thus, taking into account the alarming increase of antibiotic-resistant bacteria, the added ability of pathogens to reside within the protection of the biofilm matrix all too often makes effective treatment of these infections impossible.

Targeting EPS exopolysaccharides. In the majority of biofilms, microorganisms make up less than 10% of the dry mass, while the EPS represents more than 90%, with polysaccharides often being a major constituent [8]. These polysaccharides provide a variety of functions crucial to the formation and integrity of the biofilm, including but not limited to: initial surface adhesion, aggregation of bacterial cells, water retention, mechanical stability, sorption of nutrients and ions, nutrient storage, binding of enzymes, and serve as a protective barrier against antimicrobial agents and environmental stressors [8]. Thus, active degradation of polysaccharides may prove to be a promising, universally applicable approach to clinically addressing biofilm infections. Glycoside hydrolases (GHs) are enzymes that act by hydrolyzing the glycosidic linkages between two or more carbohydrates [9]. They can be individually characterized by the specific type of linkage that they cleave, such as $\alpha$-1,4 bond hydrolysis by $\alpha$-amylase, $\beta$-1,4 bond hydrolysis by cellulase, or $\beta$-1,3 bond hydrolysis by $\beta$-1,3 galactosidase (FIG. 1) [10, 11]. Considering the important contribution of polysaccharides to the biofilm architecture, it has been hypothesized that hydrolyzing the glycosidic linkages that hold them together will lead to degradation of the EPS. Indeed, microorganisms themselves utilize specific glycoside hydrolases to initiate dispersal events. For example, dispersin B is a $\beta$-hexosaminidase produced by the Gram-negative bacterium, *Aggregatibacter actinomycetemcomitans*, in order to disperse adherent cells from a mature biofilm [12]. It has been shown that exogenous addition of dispersin B is capable of preventing and disrupting biofilms, in vitro and in vivo [13-17].

The polysaccharide structure of multiple, biofilm-producing, bacterial pathogens has been elucidated [18-20]. One glycosidic linkage commonly seen within the exopolysaccharides secreted by a wide range of pathogens is the $\beta$-1,4 bond, such as that present in cellulose, an exopolysaccharide produced by many strains of *E. coli, Salmonella, Citrobacter, Enterobacter, Pseudomonas*, and more [21]. Cellulase is a commercially available enzyme that hydrolyzes these $\beta$-1,4 linkages [22], and thus could theoretically serve to break up a host of biofilm exopolysaccharides into simple sugars. It has been shown that cellulase inhibits biofilm growth by *Burkholderia cepacia* and *Pseudomonas aeruginosa* on various abiotic surfaces commonly used in medical devices [22, 23]. Similarly, Alpha-amylase, a GH that acts by cleaving the $\alpha$-1,4 straight-chain linkage, has been previously shown to inhibit the biofilm formation of, as well as disrupt the pre-formed biofilms of, *Vibrio cholerae, Staphylococcus aureus* and *P. aeruginosa*, in vitro [24-26]. In this study, the inventors sought to hydrolyze the polysaccharides produced by *S. aureus* and *P. aeruginosa* in dual-species polymicrobial biofilms by targeting a pair of highly conserved glycosidic linkages. The inventors focused on *S. aureus* and *P. aeruginosa* because they are the two most commonly isolated bacterial species in CWIs, and are often found together in polymicrobial infections [27, 28]. It was found that α-amylase and cellulase were able to disrupt *S. aureus* and *P. aeruginosa* biofilms, leading to increased dispersal and antibiotic efficacy.

Bacterial strains. *P. aeruginosa* strain PAO1 [29] and *S. aureus* strain SA31 [30] have been previously described. *S. aureus* and *P. aeruginosa* were grown in baffled Erlenmeyer flasks, with shaking at 200 rpm, in Luria-Bertani (LB) broth at 37° C. Planktonically grown cells were then used to initiate infection in the in vitro and in vivo models. All colony forming units (CFU) were quantified by serial dilution and 10 µL spot-plating on *Staphylococcus* Medium 110 (Difco™) and *Pseudomonas* Isolation Agar (Difco™)

Glycoside hydrolases. Bacterial alpha-amylase (from *Bacillus subtilis*; MP Biomedicals, LLC #02100447) and fungal cellulase (from *Aspergillis niger*; MP Biomedicals, LLC #02150583) were utilized for these experiments. All enzymes were prepared by dissolving lyophilized powder in either double-distilled water (ddH2O), or 1× phosphate-buffered saline (PBS) at 65° C. for 5 minutes. Heat-inactivated controls were generated by heating the enzyme solutions at 95° C. for 20 minutes.

Crystal violet assay. A traditional in vitro crystal violet (CV) biomass assay [31] was performed by inoculating the wells of a 24-well non-tissue culture treated plate (Falcon®) containing 13 mm plastic cell culture coverslips with 1:100 dilutions of overnight cultures of *S. aureus* and *P. aeruginosa* in fresh LB broth, and allowing for 48 hours of growth at 37° C., with shaking at 80 rpm. Planktonic cells were then removed via rinsing with PBS, and the biofilm-coated coverslips were treated with enzyme solutions, vehicle, or heat-inactivated controls. After treatment, the coverslips were rinsed with ddH2O, and the remaining biomass was stained with 1% CV in ddH2O for 20 minutes. Coverslips were then rinsed once more with ddH2O and transferred to fresh wells, in which the CV was eluted in 95% ethanol for 1 hour. The eluted CV from treated vs. untreated samples was quantified via absorbance of 595 nm light in a Synergy H1 Hybrid Reader (Biotek®).

In vitro cell dispersal. To measure percent dispersal in vitro, the wells of a 24-well non-tissue culture treated plate (Falcon®) were inoculated with 1:100 dilutions of overnight cultures of *S. aureus* and *P. aeruginosa*, and biofilms were allowed to grow for 48 hours at 37° C., with shaking at 80 rpm. Following incubation, the supernatant was removed, and each well was gently rinsed with PBS to discard any non-attached biomass. Subsequently, wells were treated with enzyme solutions, vehicle, or heat-inactivated controls. Following treatment, the supernatant was removed and centrifuged at 11,000 rcf for 10 minutes in order to pellet the cells. Cell pellets were then re-suspended in PBS for CFU quantification. Biofilm remaining on the wells were dispersed via sonication and suspended in PBS for CFU quantification. Percent bacterial cell dispersal was calculated by finding the quotient of the total CFU (biofilm-associated plus planktonic) divided by the planktonic CFUs (in the supernatant).

Lubbock Chronic Wound Biofilm Model. The Lubbock Chronic Wound Biofilm Model, or Lubbock wound model (LWM), has been previously described [Sun Y, Dowd S E, Smith E, Rhoads D D, Wolcott R D. In vitro multispecies Lubbock chronic wound biofilm model. Wound Repair Regen. 2008; 16(6):805-13. Epub 2009/01/09. DeLeon S, Clinton A, Fowler H, Everett J, Horswill A R, Rumbaugh K P. Synergistic interactions of *Pseudomonas aeruginosa* and *Staphylococcus aureus* in an in vitro wound model. Infect Immun. 2014; 82(11):4718-28. Epub 2014/08/27. Dalton T, Dowd S E, Wolcott R D, Sun Y, Watters C, Griswold J A, et al. An in vivo polymicrobial biofilm wound infection model to study interspecies interactions. PLoS One. 2011; 6(11): e27317. Epub 2011/11/15, relevant portions incorporated herein by reference]. Briefly, wound-like media (50% bovine plasma, 45% Bolton broth, 5% laked horse blood) was inoculated with 105 bacterial cells, and incubated for 48 hours, statically, at 37° C. Following incubation, the resulting biofilms were extracted, weighed and treated with a vehicle control (ddH2O), GH, or GH plus antibiotics. Percent bacterial cell dispersal was calculated by finding the quotient of the total CFU (biofilm-associated plus planktonic) divided by the planktonic CFUs (in the supernatant). Percent biomass degraded was calculated by rinsing to remove the post-treatment supernatant, weighing the remaining biomass, and finding the quotient of the post-treatment biofilm weight divided by the pre-treatment biofilm weight. Percent antibiotic tolerance was obtained by treating biofilms with GH, or GH plus antibiotic, and finding the quotient of the antibiotic-treated biofilm CFUs/gram divided by the GH only-treated biofilm CFUs/gram.

Murine chronic wound model. A murine chronic wound model has been previously described [Dalton T, Dowd S E, Wolcott R D, Sun Y, Watters C, Griswold J A, et al. An in vivo polymicrobial biofilm wound infection model to study interspecies interactions. PLoS One. 2011; 6(11):e27317. Epub 2011/11/15. Brown R L, Greenhalgh D G. Mouse models to study wound closure and topical treatment of infected wounds in healing-impaired and normal healing hosts. Wound Repair Regen. 1997; 5(2):198-204. Epub 1997/04/01. Rumbaugh K P, Diggle S P, Watters C M, Ross-Gillespie A, Griffin A S, West S A. Quorum sensing and the social evolution of bacterial virulence. Curr Biol. 2009; 19(4):341-5. Epub 2009/02/24, relevant portions incorporated herein by reference]. Briefly, mice were anesthetized by intraperitoneal injection of sodium pentobarbital. After a surgical plane of anesthesia was reached, the backs were shaved and administered a full-thickness, dorsal, 1.5× 1.5 cm excisional skin wound to the level of panniculus muscle with surgical scissors. Wounds were then covered with a semipermeable polyurethane dressing (OPSITE dressing; Smith & Nephew®), under which 104 bacterial cells were injected into the wound-bed. Biofilm formation was allowed to proceed for 72 hours, after which the mice were euthanized, and the wound-beds were harvested for ex vivo treatment with vehicle control, GH alone, or GH plus antibiotic. Percent dispersal, percent biomass degraded, and antibiotic tolerance were calculated as with the LWM, described above.

Figure 2:
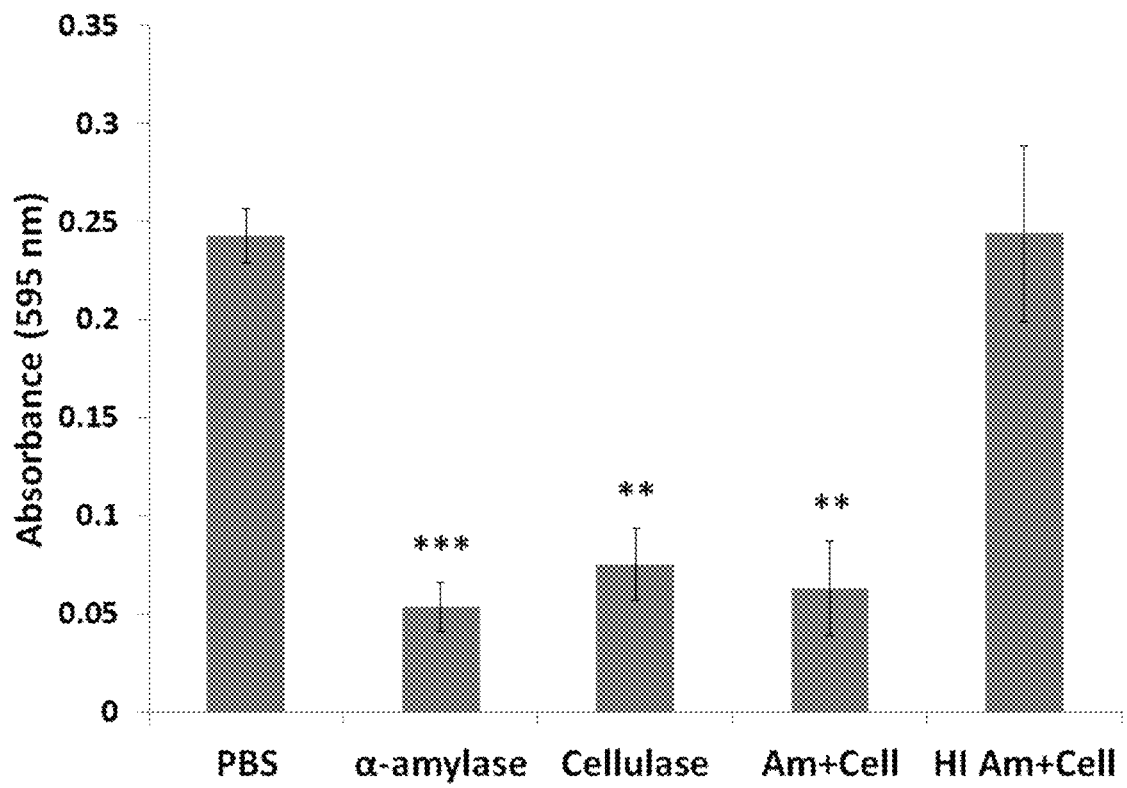
FIG. 2 is a graph that shows that glycosidic hydrolases (GHs) reduce the biomass of polymicrobial biofilms. Traditional crystal violet biofilm assays were performed after 48 hours of co-culturing S. aureus and P. aeruginosa. Planktonic cells were removed and biofilms were treated with 0.25% GH solutions (α-amylase, cellulase, or α-amylase+cellulase [Am+Cell]), vehicle, or heat-inactivated [HI] controls for 30 minutes before staining with 1% crystal violet. One-way ANOVA and the Tukey-Kramer multiple-comparison test were used to test for differences between columns: *$p<0.001$, $p<0.01$.
Figure 3A:
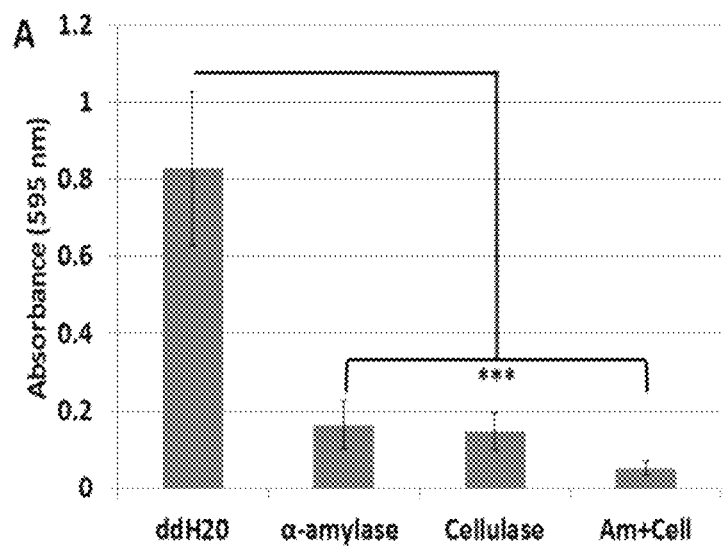
FIGS. 3A and 3B show that α-amylase degrades S. aureus+P. aeruginosa biofilms in vitro. Traditional crystal violet biofilm assays (1) were performed after 48 hours of co-culturing S. aureus and P. aeruginosa (FIG. 3A) 0.0025% α-amylase, cellulase, and a 1:1 combination of both [Am+Cell] significantly degraded pre-formed S. aureus and P. aeruginosa biofilms in 10 minutes.
Figure 3B:
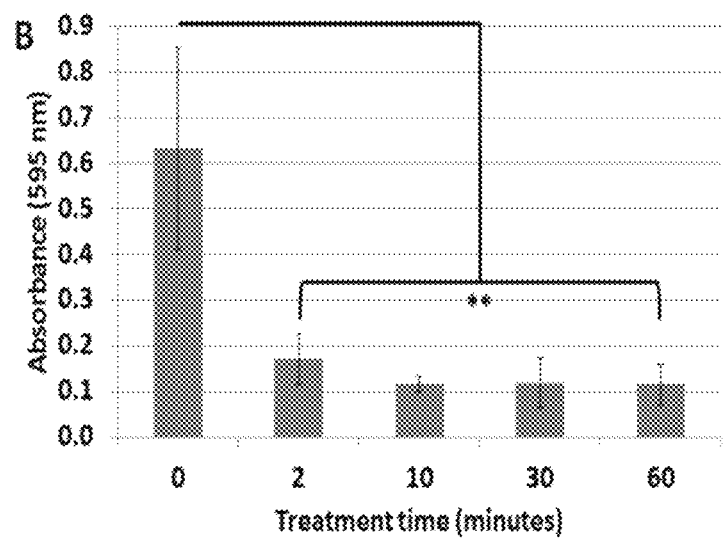

Glycoside hydrolase treatment reduces biofilm biomass and increases bacterial dispersal. The ability of α-amylase and cellulase to disrupt *S. aureus* and *P. aeruginosa* biofilms that were grown on plastic cell culture coverslips was tested. After 48 of bacterial growth, the biofilm-coated coverslips were treated with a 0.25% GH solution for 30 minutes and the biomass of the biofilms was estimated by the retention of crystal violet stain (FIG. 2). A significant reduction in biomass was observed after treatment with both GHs, but not GH that had been heat-inactivated. Significant degradation was seen at concentrations as little as 0.0025%, and at treatment times as short as 2 minutes (FIGS. 3A and 3B).

Figure 4:
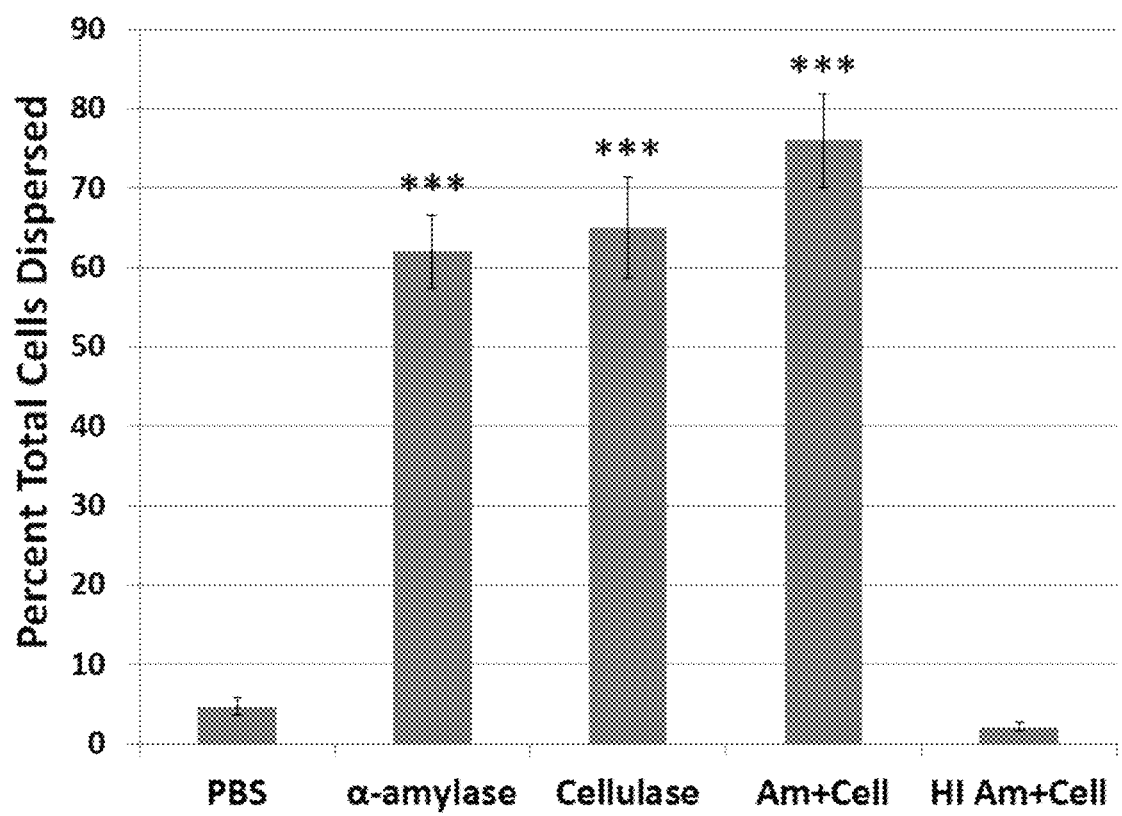
FIG. 4 is a graph that shows that GHs disperse bacterial cells in vitro. 48 hr. old S. aureus and P. aeruginosa biofilms were treated with 5% GH solutions (α-amylase, cellulase, or amylase+cellulase [Am+Cell]), vehicle, or heat-inactivated controls [HI] for 30 minutes. Percent dispersal was calculated as follows: (CFU in supernatant)/(CFU in supernatant+CFU remaining in biofilm). One-way ANOVA and the Tukey-Kramer multiple-comparison test were used to test for differences between columns: ***$p<0.001$. Note: Am+Cell was not significantly greater that either α-amylase or cellulase alone.
Figure 5:
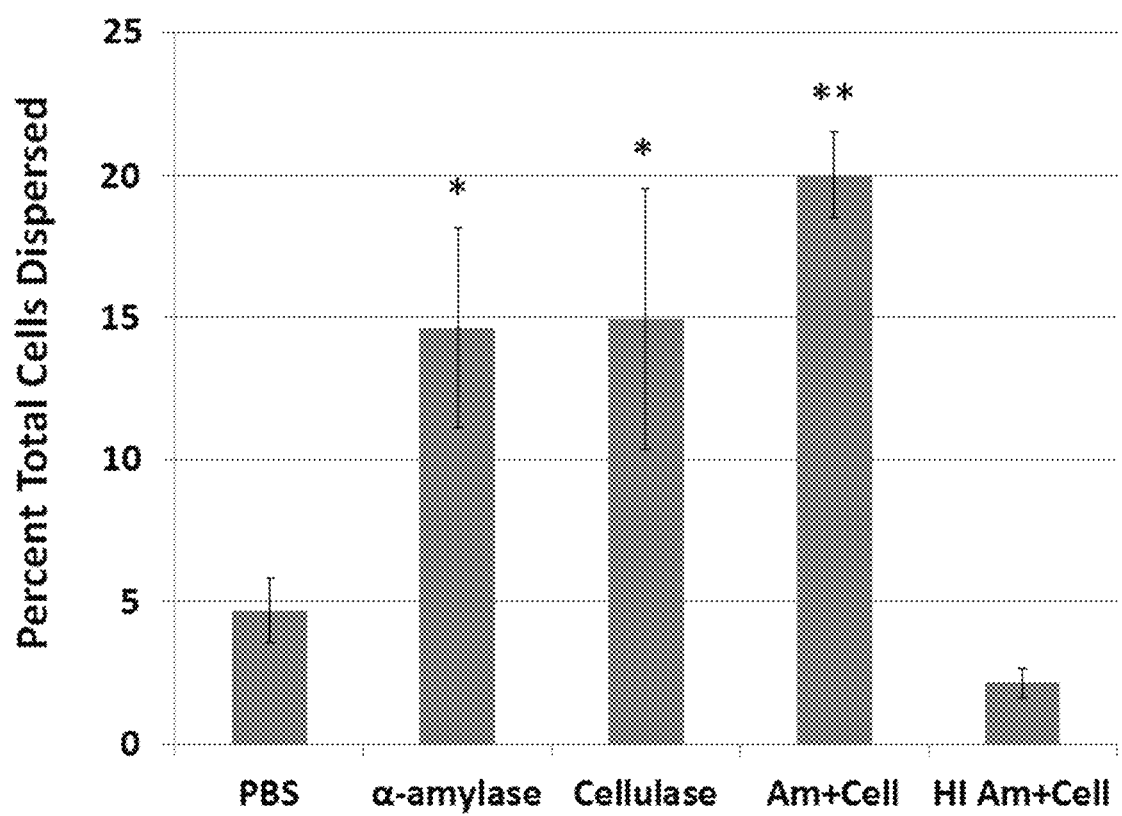
FIG. 5 is a graph that shows that GHs disperse bacterial cells in vitro at low concentrations. Wells were inoculated with co-cultures of S. aureus and P. aeruginosa and incubated for 48 hours. Then, wells were treated with 0.25% GH solutions (α-amylase, cellulase, or amylase+cellulase [Am+Cell]), vehicle, or heat-inactivated controls [HI] for 30 minutes. Percent dispersal was calculated as follows: (CFU in supernatant)/(CFU in supernatant+CFU remaining in biofilm). One-way ANOVA and the Tukey-Kramer multiple-comparison test were used to test for differences between columns: **$p<0.01$, *$p<0.05$. Note: Am+Cell was not significantly greater that either α-amylase or cellulase alone.

Given the degradation of biofilm biomass, it was expected that the biofilm-associated cells would be dispersed into their planktonic state due to loss of EPS structure. An in vitro well-plate dispersal assay was performed to measure total cell dispersal. *S. aureus*+*P. aeruginosa* co-culture biofilms, grown in the wells of a non-tissue culture treated plate, were treated with 5% GH solutions and the percentage of total cells that were dispersed into the supernatant was calculated. α-amylase, cellulase, and a 1:1 solution of both, all resulted in a significant amount of dispersal when compared to vehicle and heat-inactivated controls (FIG. 4). 0.25% concentration solutions, like those utilized in the crystal violet assays, also resulted in significant, albeit lesser, dispersal (FIG. 5).

Figure 6:
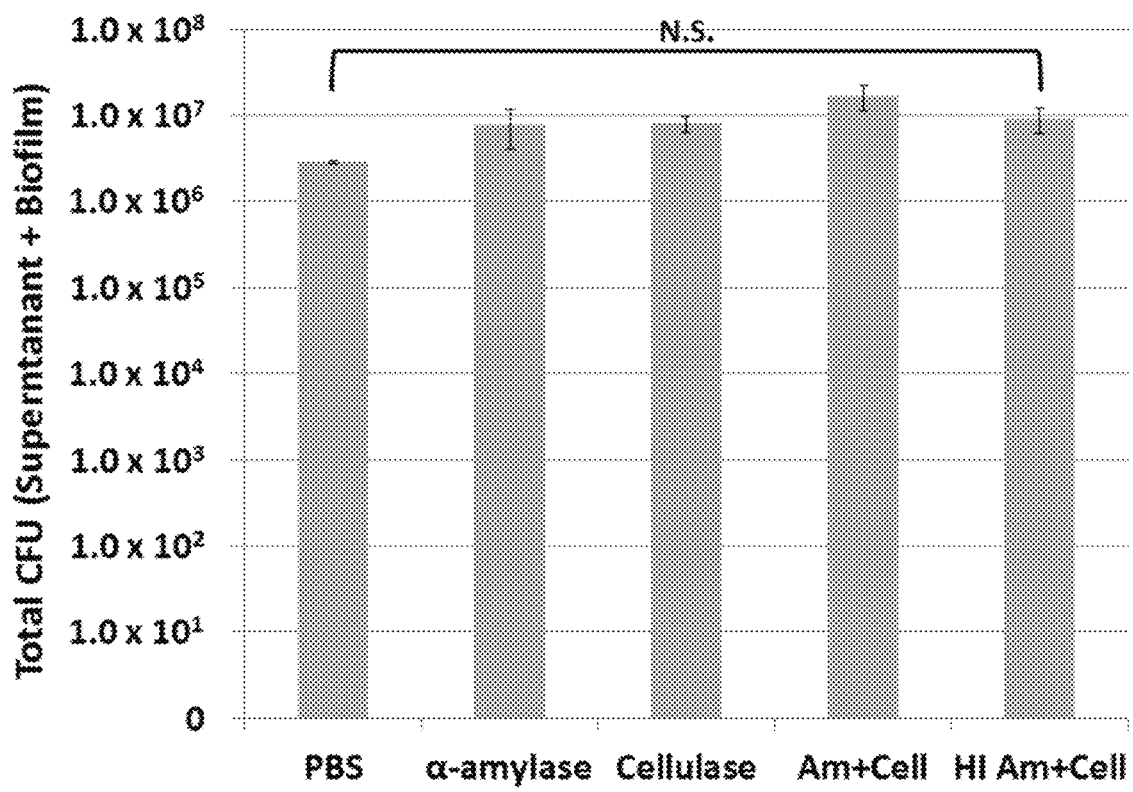
FIG. 6 is a graph that shows that GH treatment has no bactericidal activity in vitro. Wells were inoculated with co-cultures of S. aureus and P. aeruginosa and incubated for 48 hours. Then, wells were treated with 5% GH solutions (α-amylase, cellulase, or amylase+cellulase [Am+Cell]), vehicle, or heat-inactivated controls [HI] for 30 minutes. Total CFU was then calculated (CFU in supernatant+CFU remaining in biofilm) for all treatment types and compared. One-way ANOVA and the Tukey-Kramer multiple-comparison test were used to test for differences between columns (N.S.=not significant).

While the bacterial population started off with roughly equal numbers of P. aeruginosa and S. aureus, by 24 hours P. aeruginosa represented most of the population. This is likely due to the production of several virulence factors by P. aeruginosa, which are lethal to S. aureus [38]. Prior work by the present inventors found that when the two were in vivo (and in wound-like, in vitro conditions), the CFU counts for the two bacterial species were roughly equal. It should also be noted that the overall number of CFU present (in supernatant+biofilm) in all treatment groups did not differ significantly (FIG. 6). Only the percentage of total cells present in the supernatant after GH treatment was significantly shifted, indicating that GHs do not appear to have any bactericidal activity, but simply break down biofilm.

Figure 7A:
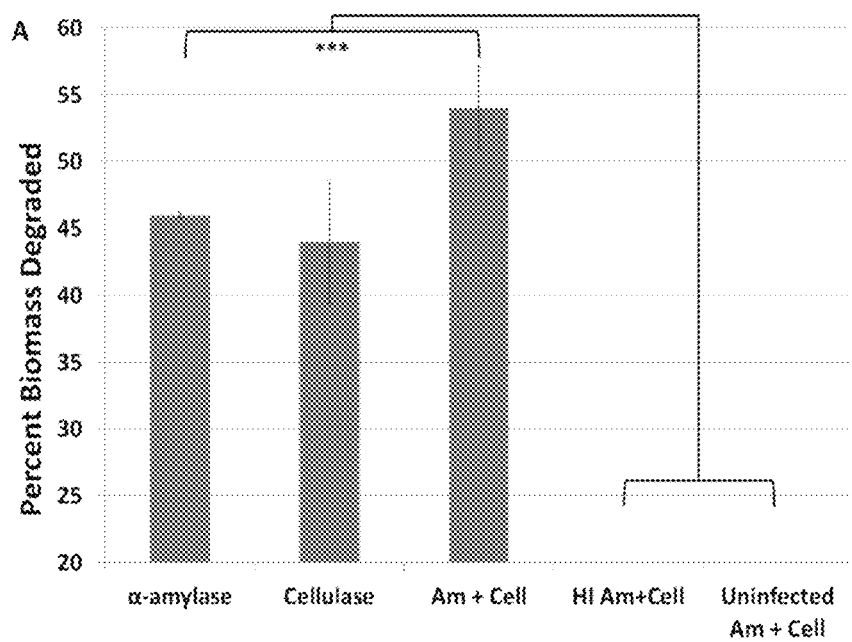
FIGS. 7A and 7B are graphs that show that GHs degrade and disperse bacterial cells ex vivo. Tissue was extracted from the wounds of mice co-infected with S. aureus and P. aeruginosa and treated with α-amylase, cellulase, or both [Am+Cell] and compared to heat-inactivated [HI] and/or uninfected controls. Extracted tissue was suspended in 5% enzyme solutions for 1 hour.
Figure 7B:
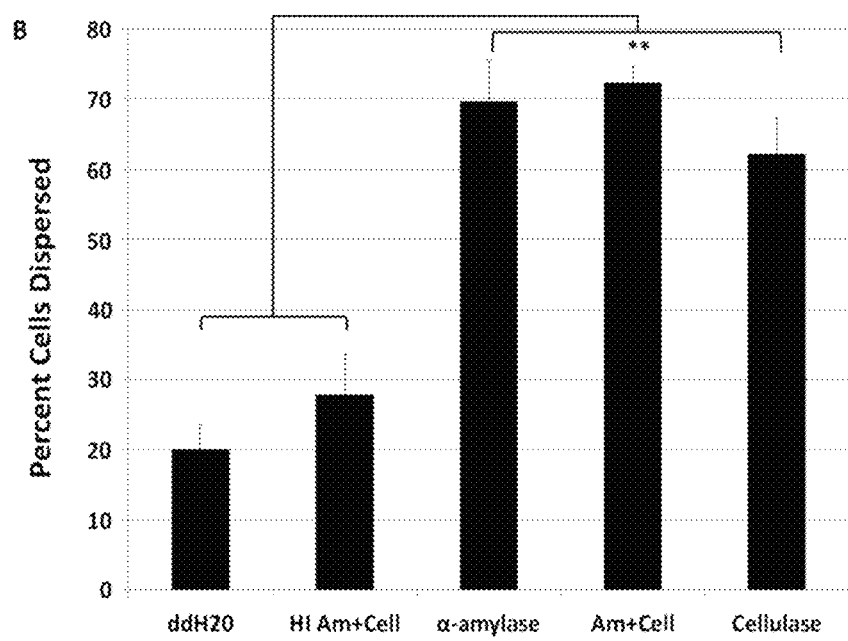

In order to determine if the results obtained in vitro translated to a more clinically relevant model, the inventors tested the ability of GH solutions to degrade the biomass of, and disperse the cells from, biofilms grown in vivo. A murine chronic wound infection model was utilized, and wounds were co-infected with S. aureus and P. aeruginosa. Briefly, after anesthesia, 1.5 cm×1.5 cm full-thickness wounds were administered on the dorsal surface of mice and covered with a transparent, adhesive bandage, under which the bacteria were injected. At 3 days post-infection, the inventors extracted the biofilms from the wound-beds and treated them with GHs. For analysis of biomass degradation, the inventors measured the weights of the extracted woundbeds before and after treatment with GH, and compared the percent reduction in weight to that of biofilms treated with heat-inactivated GH. The inventors found that α-amylase and cellulase, both alone and in a 1:1 mixture, were able to degrade S. aureus and P. aeruginosa polymicrobial biofilms harvested from murine chronic wounds (FIG. 7A). It should be noted that biomass loss in the heat-inactivated control is likely due to osmosis-powered diffusion into the distilled water over the one hour of treatment time. To test whether GHs had any degradative effects on tissue alone, the inventors performed the same GH treatment on uninfected connective tissue extracted from the wound-beds of mice, and saw no reduction in their weight due to treatment (FIG. 7A). This indicates that GH treatment causes the dissolution of up to half of the weight of the material present in the woundbeds of infected (but not uninfected) mice. To determine whether this reduction in biomass correlated with bacterial cell dispersal, the inventors also calculated the numbers of viable bacteria that were located in the treatment solution versus in the remaining biofilm after treatment with active or heat-inactivated GH. It was found that α-amylase, cellulase, and a 1:1 solution of α-amylase and cellulase resulted in significantly more total cell dispersal than vehicle and heat-inactivated controls (FIG. 7B). Cell dispersal into the control solutions was likely due to osmosis over the one hour treatment time, as mentioned above for biomass degradation.

Taken together, these results indicate that hydrolysis of glycosidic linkages of EPS exopolysaccharides by α-amylase and cellulase leads to degradation of mature biofilms grown in vitro and in vivo, and that this degradation leads to the dispersal, or planktonic release, of biofilm-resident bacterial cells.

Figure 8A:
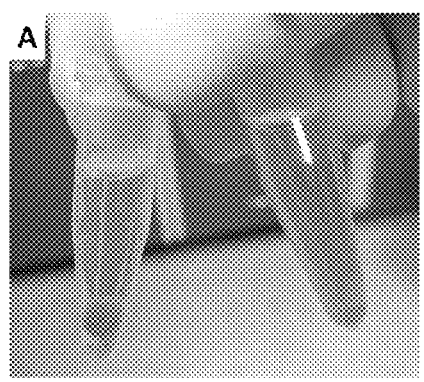
FIGS. 8A and 8B show that GHs degrade biofilms and improve the efficacy of antibiotics in vitro.
Figure 8B:
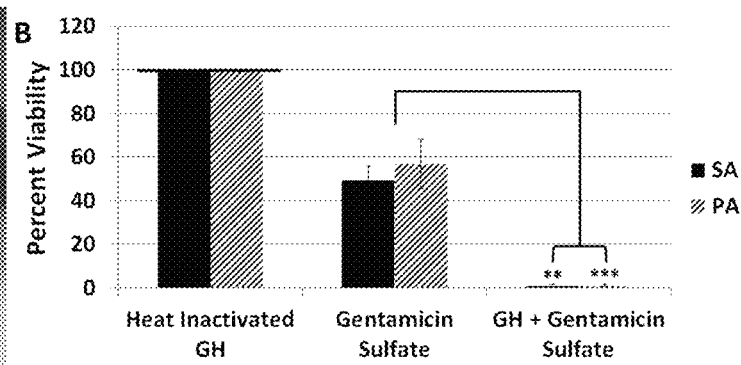
Figure 9:
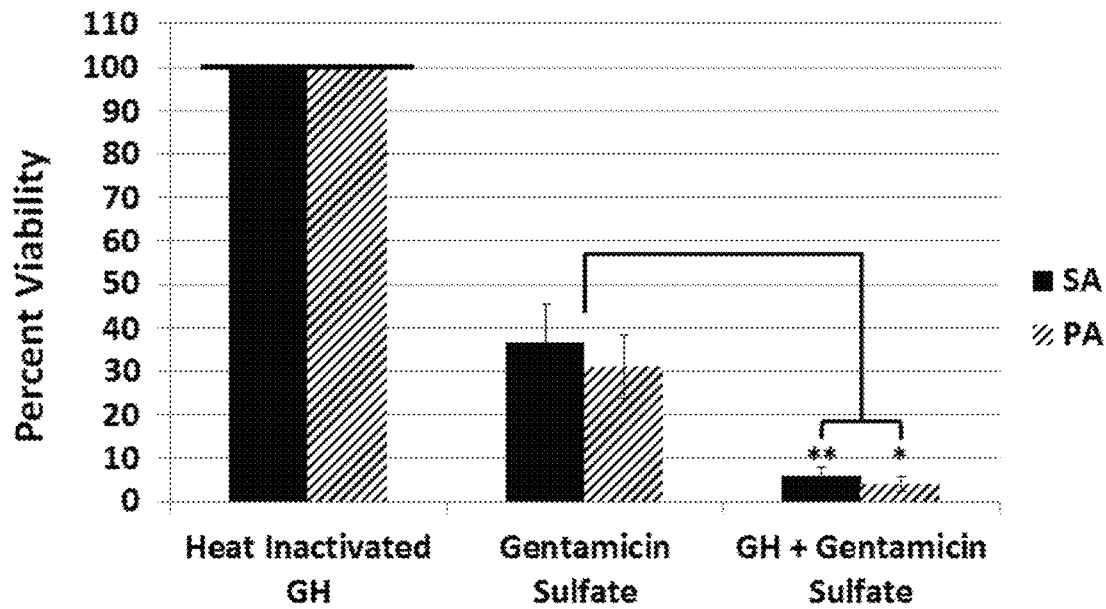
FIG. 9 is a graph that shows that GHs improve the efficacy of antibiotics ex vivo. Treatment of murine chronic wound biofilms with 5% α-amylase+5% cellulase+200 μg/mL gentamicin sulfate was more effective at killing S. aureus and P. aeruginosa than gentamicin alone. One-way ANOVA and the Tukey-Kramer multiple-comparison test were used to test for differences between columns: **$p<0.01$, *$p<0.05$.

Glycoside hydrolase therapy increases antibiotic efficacy. Bacterial cells residing within the protection of a biofilm are thought to exhibit greater tolerance to antibiotics due to the inability of certain drugs to penetrate the EPS, and to the sessile, dormant nature that many biofilm-dwelling bacteria adopt [39]. Thus, the inventors would expect dispersed, planktonic cells, resulting from GH treatment, to be more susceptible to antibiotics. To begin testing this, the inventors utilized the LWM, a clinically relevant, in vitro wound-like model [32-34], in which the inventors inoculated S. aureus and P. aeruginosa. After 48 hours of growth, the resulting biofilms were extracted and treated with either antibiotic alone, or antibiotic plus GH, and the post-treatment CFUs were enumerated and compared to those of the heat-inactivated control. It was found that a 1:1 mixture of α-amylase and cellulase increased the efficacy of gentamicin sulfate against biofilm-resident bacteria, when compared to gentamicin sulfate alone (FIGS. 8A, 8B). Gentamicin sulfate was used because it is a positively charged aminoglycoside, and it has been shown that positively charged antibiotics are less-able to penetrate the largely negatively charged biofilm EPS [40]. This makes aminoglycosides ideal for studying changes in antibiotic efficacy due to EPS destruction. The inventors have previously seen that approximately half of P. aeruginosa and S. aureus cells remain viable after gentamicin treatment when they are co-cultured together in the LWM [33], and that finding was consistent in these experiments. It was also found that a GH pre-treatment significantly increased the efficacy of gentamicin (FIG. 9). Taken together, these data show that degradation of EPS polysaccharides with GH significantly increases the ability of antibiotics to act upon the resident bacteria by dispersing the cells from the protection of the biofilm.

The ability of pathogens to exist within the protection of a biofilm poses wide-reaching complications to the ability to successfully clear infections. In particular, CWIs, such as diabetic foot ulcers, are significantly more recalcitrant and recurrent when harboring a biofilm infection [6, 37, 41, 42]. As exopolysaccharides represent a substantial and important constituent of many bacterial biofilms and contribute to both the physical and chemical stability of the EPS [8], their degradation should disperse bacteria into their planktonic state and may afford the host improved healing abilities by increasing the access of the host immune system, and administered antimicrobials/antibiotics, to the cells.

Several studies have shown the ability of exogenous GHs to inhibit biofilm formation and disrupt mature biofilms. Recently, Baker et al. showed that GHs specific for the polysaccharides Pel and Psl are capable of preventing the formation of, and degrading P. aeruginosa biofilms in vitro, as well as potentiating antibiotics and increasing the ability of neutrophils to kill the bacteria [43]. However, to my knowledge GHs have not, until now, been tested against biofilms grown in vivo. Ideally, GHs to be used clinically would exhibit broad efficacy against a variety of polysaccharides produced by vastly different species of pathogens, especially considering the complex polymicrobial nature of most infections [44]. Therefore, it stands to reason that GHs that target highly conserved glycosidic linkages would be highly advantageous. In this way, clinicians would be able to administer the enzymes to any patient presenting with a biofilm infection, regardless of the causative microorganisms, and have a reasonable expectation that the therapy will be effective. α-amylase and cellulase are two inexpensive, commercially available GHs that target common linkages found in the EPS made by many different species of bacteria, and multiple studies have shown that they can inhibit and disrupt the pre-formed, in vitro biofilms of a variety of bacterial species [22-26].

Example 2. Consequences of Biofilm Dispersal on the Host

Chronic biofilm infections. Chronic infections are often exacerbated by the presence of a biofilm, a complex community of microorganisms living within a matrix of polysaccharides, proteins, eDNA, lipids and other molecules that comprise the extracellular polymeric substance (EPS). Living within the protection of the EPS, one or multiple species of microbes are afforded greatly increased tolerances to both antimicrobials and host defenses [1, 2]. These biofilm-afforded tolerances are due to several proposed mechanisms, involving physical and chemical protection from both host-derived and exogenous antimicrobials. Additionally, the varying degrees of bacterial metabolic inactivity within the biofilm greatly influences susceptibility to antibiotics, the majority of which depend on active metabolism [3]. Thus, biofilm infections, which have been estimated to comprise as much as 80% of all human bacterial infections, including greater than 90% of all chronic wound infections [4, 5], are highly recalcitrant and resilient to traditional therapies.

EPS targeting. As an alternative approach to directly targeting the causative pathogens of a biofilm infection, many researchers have redirected their efforts towards EPS matrix constituents [6]. In theory, dispersal of biofilm microbes into their planktonic form will increase their susceptibility to antimicrobials and the host immune system. Further, because they do not directly target the microorganisms themselves, they should be less likely to drive resistance. To date, a host of EPS-specific dispersal agents have been investigated, with targets including, but not limited to, structural exopolysaccharides, exoproteins, and eDNA [3, 6]. However, it should be noted that clinical application of such therapies are virtually non-existent, with the exception of Dornase alpha (Pulmozyme®) as an FDA-approved therapy for the breakup of DNA-rich mucus presenting in cystic fibrosis patients [7, 8], but which also may be active on biofilms in the lungs. While medically induced dispersal of a mature biofilms in vivo has yet to be demonstrated, EPS-targeting, especially enzymatic-mediated deconstruction of matrix constituents, represents a promising antibiofilm avenue.

Exopolysaccharide targeting by glycoside hydrolases. Exopolysaccharides are one of the major structural components for the majority of EPS producers [9]. They play a variety of vital roles in biofilm formation and persistence, including but not limited to: surface and cell-cell adhesion and aggregation, tolerance to desiccation, mechanical stability, nutrient sorption and storage, binding of enzymes, and physical protection against antimicrobials and the environment [9]. Considering their ubiquity and importance to the structural integrity of the EPS matrix, active degradation of exopolysaccharides represents a promising approach to clinically eradicating biofilm infections.

Glycoside hydrolases (GHs) are enzymes that act by hydrolyzing the glycosidic linkages between two or more carbohydrates [10]. They can be individually characterized by the specific type of linkage that they cleave, such as α-1,4 bond hydrolysis by α-amylase, β-1,4 bond hydrolysis by cellulase, or β-1,3 bond hydrolysis by β-1,3 galactosidase [11, 12]. Moreover, by targeting common, highly conserved glycosidic linkages, a single therapy can potentially prove efficacious against the EPS produced by a broad-spectrum of pathogens, and against the highly complex and compositionally chimeric polymicrobial biofilms often seen clinically [13]. Additionally, GHs are unlikely to pose significant risk to the patient, being that their targets (glycosidic linkages) are not readily found in human tissue.

The effects of dispersal on the host. As shown hereinabove, GH therapy using a dual-enzyme combination of α-amylase and cellulase resulted in significant reductions in biomass, and the dispersal of biofilm-dwelling bacteria, allowing for an increase in the effectiveness of antibiotic treatments in vitro and ex vivo [14]. However, it has been hypothesized that triggering a large-scale dispersal event in a living host can overwhelm the immune system, causing dissemination of the infection and possibly lethal septicemia [15]. To my knowledge, dispersal-induced septicemia has never been demonstrated, and in this study the inventors show that: 1) large-scale dispersal can result in a lethal septic event; 2) this septicemia appears to be dependent on the motility of the bacteria; 3) the probability of death by septicemia is positively correlated to wound size; 4) concurrent systemic and topical antibiotics can protect the host against septicemia; and/or 5) GH therapy augments the ability of antibiotic intervention to clear the infection.

Bacterial strains. *P. aeruginosa* wild-type strains PAO1 [16] and MPAO1 [17], *S. aureus* strain SA31 [18], PAO1:: pelpsl [19], a MPAO1::flgK transposon mutant (PW2960; PA1086-F09::ISlacZ/hah) [17], and a bioluminescent PAO1 strain carrying the luminescence reporter plasmid pQF50-lux [20] have been previously described. All *S. aureus* and *P. aeruginosa* strains were grown in baffled Erlenmeyer flasks, with shaking at 200 rpm, in Luria-Bertani (LB) broth at 37° C. Planktonically grown cells were then used to initiate infection in the in vitro and in vivo models. All colony forming units (CFU) were quantified by serial dilution and 10 μL spot-plating on *Staphylococcus* Medium 110 (Difco™) and *Pseudomonas* Isolation Agar (Difco™)

Glycoside Hydrolases. Bacterial alpha-amylase (from *Bacillus subtilis*; MP Biomedicals) and fungal cellulase (from *Aspergillis niger*; MP Biomedicals) were utilized for these experiments. Briefly, powdered enzymes were dissolved in phosphate-buffered saline to achieve the desired percentage concentration (w/v). Heat inactivation was performed by heating the enzyme solutions for 25 minutes at 90° C.

Mouse model. A murine chronic wound model was described hereinabove. Briefly, mice were anesthetized by intraperitoneal injection of sodium pentobarbital. After a surgical plane of anesthesia was reached, the backs were shaved and administered a full-thickness, dorsal excisional skin wound to the level of panniculus muscle with surgical scissors. Wounds were then covered with a semipermeable polyurethane dressing (OPSITE dressing; Smith & Nephew®), under which 104 bacterial cells were injected into the wound-bed. Biofilm formation was allowed to proceed for 48-72 hours, a time at which the inventors have demonstrated the presence of biofilm in wounds.

Glycoside hydrolase and antibiotic treatments. Established infections were treated via topical application of vehicle control, heat-inactivated GH, antibiotic alone (or in combination with heat-inactivated GH), GH alone, or GH plus antibiotic (meropenem). Briefly, woundbeds were irrigated with a 10% α-amylase and cellulase (in a 1:1 combination) solution in three separate topical infusions with 30 minutes of dwell time for each, with or without antibiotics. Septicemia was determined by monitoring animals for signs of systemic illness (lethargy, loss of appetite, labored breathing, tremors), and moribund mice were euthanized via phenobarbital injection. In vivo cell dispersal was determined by collecting the dispersed cells in the post-treatment irrigation solution, plating on selective agar, and quantifying cells dispersed by treatment vs. control solutions. In order to image dispersal in vivo, the inventors used a Lumina II XR In Vivo Imaging System (IVIS®). Mice with established wound infections were administered GH therapy, and imaging occurred immediately following treatment, and every 4-5 hours subsequently. For experiments involving systemic antibiotic therapy, peritoneal dosing of 300 mg/kg meropenem occurred 4 hours prior to, and 8 hours following GH treatment. For topical antibiotic therapy, 5 mg/mL meropenem was added to the GH or control treatment solutions.

Figure 10:
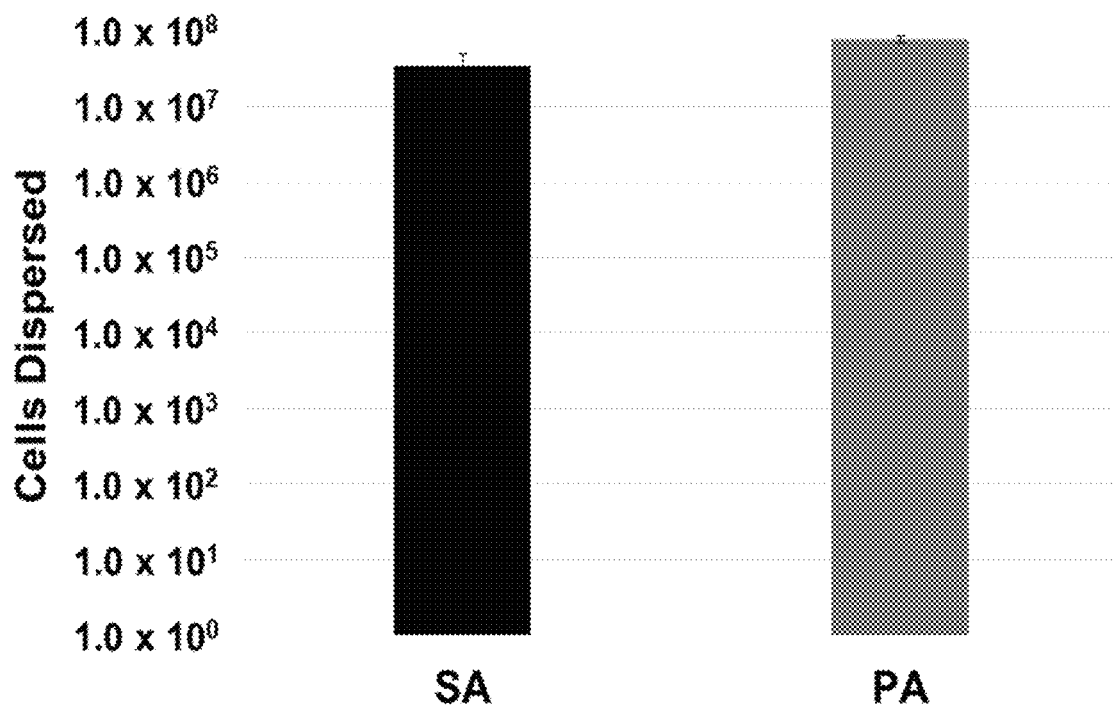
FIG. 10 is a graph that shows in vivo GH-induced dispersal quantification. Treatment of 48-hour mouse chronic wounds, infected with S. aureus and P. aeruginosa, with 10% α-amylase and cellulase (1:1; GH) resulted in significant dispersal of bacterial cells from the biofilms.

GH disperses biofilms in vivo, but causes rapid septicemia. It has been hypothesized that inducing a substantial dispersal event in vivo may overwhelm the host immune system, possibly resulting in fatal septicemia [3]. When 2-day-old $P.$ $aeruginosa$ chronic wound infections were treated in situ with 10% GH, it triggered the dispersal of more than 10$^7$ cells (FIG. 10), resulting in significant septicemia within as short as 15 hours (FIG. 11). Pre-treating with 10% GH prior to inoculation did not cause an increase in septicemia, indicating that it is the effect of GH on the biofilm, on not on the host tissue or vasculature, which influences bacteremia (Table 2). When the inventors compared the dispersal-induced septicemia rates between mice infected with wild-type PAO1 and a double-polysaccharide knockout lacking Psl and Pel production (the two main polysaccharides produced by PAO1 [26]), it was found by the present inventors that total septicemia within 48 hours was equal, but that the septicemia resulting from infections with the wild-type PAO1 occurred more rapidly, despite the wound-bed bacterial loads being roughly equal (FIGS. 12A, 12B). This shows that dispersal rate is dependent on the presence of polysaccharides in the EPS matrix. It should be noted that mucoid $P.$ $aeruginosa$ strains produce a third polysaccharide, alginate. However, PAO1 is non-mucoid, and so alginate production should be low, but considering that treating the polysaccharide double-knockout still results in eventual dispersal, it is evident that some alginate is involved in the matrix.

TABLE 2

Pre-infection treatment with GH does not induce septicemia.
Treatment of mice with 10% α-amylase and cellulase (1:1; GH) prior to infection with $P.$ $aeruginosa$ did not render the animals susceptible to septicemia 3 replicate animals were used for each treatment type, and organs were harvested 48 hours later for quantification of microbial loads.

| | Spleen | Liver | Kidney |
|---|---|---|---|
| PBS 1 | 0 | 0 | 0 |
| PBS 2 | 0 | 0 | 0 |
| PBS 3 | 2.0 × 10$^3$ | 2.0 × 10$^3$ | 1.0 × 10$^3$ |
| GH 1 | 0 | 0 | 0 |
| GH 2 | 0 | 0 | 0 |
| GH 3 | 0 | 0 | 0 |

The systemic spread of bacteria appears to occur via the cardiovascular system, with detectable levels of bacteria appearing in the blood in as little as 5 hours post-treatment (data not shown). Thus, it is shown herein for the first time that fatal septicemia can be induced by large-scaled dispersal of a biofilm infection.

Figure 13:
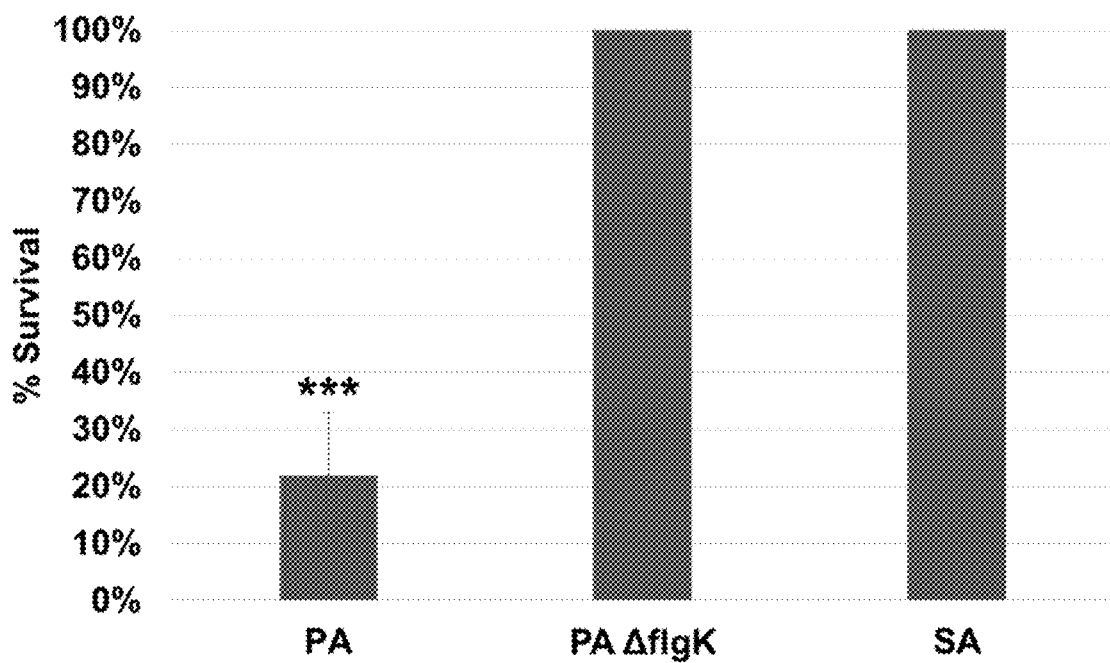
FIG. 13 is a graph that shows the swimming motility is required for dispersal-induced septicemia. Treatment of 48-hour mouse chronic wounds, infected with wild-type (PA) or a flagella mutant of P. aeruginosa, or with S. aureus (SA), with 10% α-amylase and cellulase (1:1; GH), resulted in ~80% septicemia only in mice infected with the motile strain. Repeated measures ANOVA and the Tukey-Kramer multiple-comparison test were used to test for differences between columns: ***$p<0.001$. N=9 for each group.

Dispersal-mediated septicemia is dependent upon swimming-motility. In order to investigate and characterize the pathogenesis of mortal septicemia brought on by GH-induced dispersal, the inventors investigated whether bacterial motility was correlated with increased rates of septicemia. Mouse wound beds were inoculated with the $P.$ $aeruginosa$ wild-type strain, MPAO1, a $P.$ $aeruginosa$ flagellar mutant, MPAO1:AflgK, or the non-motile Gram-positive wound pathogen, $S.$ $aureus$ (SA31), and biofilms were allowed to form over 48 hours. Wounds were then irrigated with a 10% α-amylase and cellulase (in a 1:1 combination) solution in three separate topical infusions with 30 minutes of dwell time for each. Following treatment, mice were monitored over 36 hours for septicemia. Only infection with the motile, MPAO1 wild-type strain proved fatal, with nearly 80% of the animals showing signs of septicemia (FIG. 13) after GH treatment. This difference was not due to bacterial load, as there was no significant difference between the bacterial load in mice infected with the different strains (average pre-treatment CFU/g: PA=4.33×10$^7$, PA: AflgK=3.00×10$^8$, SA=1.90×10$^7$; significance determined via one-way ANOVA and the Tukey-Kramer multiple-comparison test). Thus, swimming motility is necessary for dispersal-induced septicemia in this wound infection model.

Figure 14:
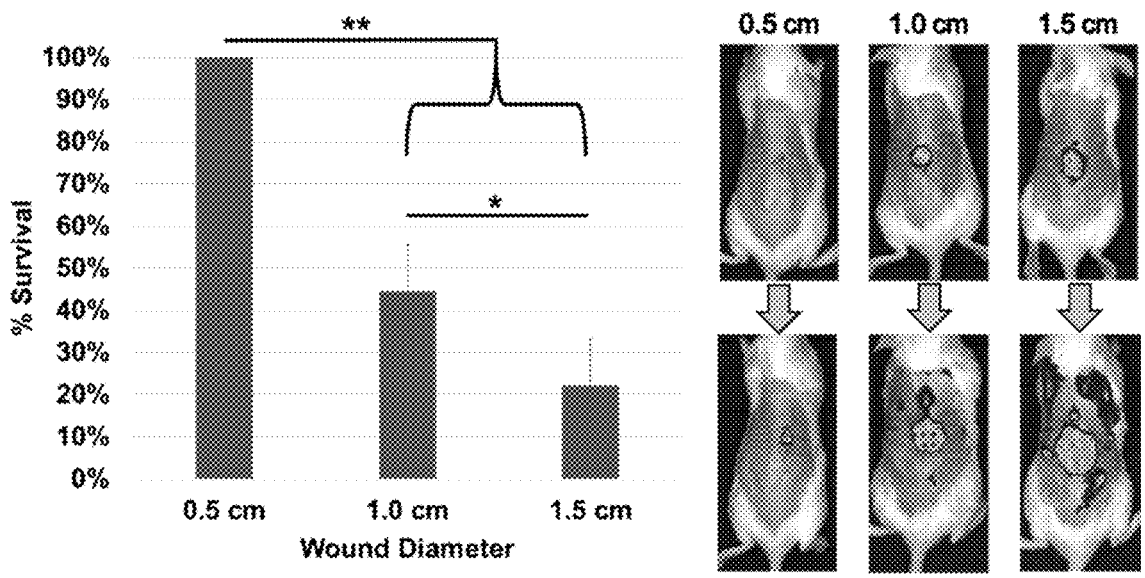
FIG. 14 is a graph with imaging that shows that wound size is positively correlated with dispersal-induced septicemia. Treatment of 48-hour mouse chronic wounds of varying sizes (0.5, 1.0, and 1.5 cm in diameter) with 10% α-amylase and cellulase (1:1; GH) resulted in no mortality in the 0.5 cm group after 36 hours, and significantly increased mortality in the 1.0 cm and 1.5 cm groups, indicating that increased wound size is correlated with septicemia. A representative mouse for each wound size is shown. Repeated measures ANOVA and the Tukey-Kramer multiple-comparison test were used to test for differences between columns: *$p<0.05$, **$p<0.01$. N=9 for each group.

Dispersal-mediated septicemia is positively correlated with wound size. To determine the effect of wound surface area on dispersal-induced septicemia, mice were administered wounds of varying diameters, including 0.5 cm, 1.0 cm, and 1.5 cm. The wounds were infected with bioluminescent $P.$ $aeruginosa$, after which biofilms were allowed to grow over 48 hours. The established infections were treated with 10% GH as above, and the animals were monitored over 36 hours for septicemia. No septicemia occurred for the smallest wound size (0.5 cm diameter), while mice with the medium wound size (1.0 cm diameter) exhibited a mortality rate of greater than 50%, and mice with the largest wound size (1.5 cm diameter) nearly 80% (FIG. 14). No significant differences in bacterial load were observed between the small and medium wounds, or between the medium and large wounds (average CFU/g: small=1.03×10$^7$, medium=5.33×10$^7$, large=2.00×10$^8$; significance determined via one-way ANOVA and the Tukey-Kramer multiple-comparison test), indicating that greater surface area, and not increased bacterial load, is more correlated to bacteremia.

Figure 15A:
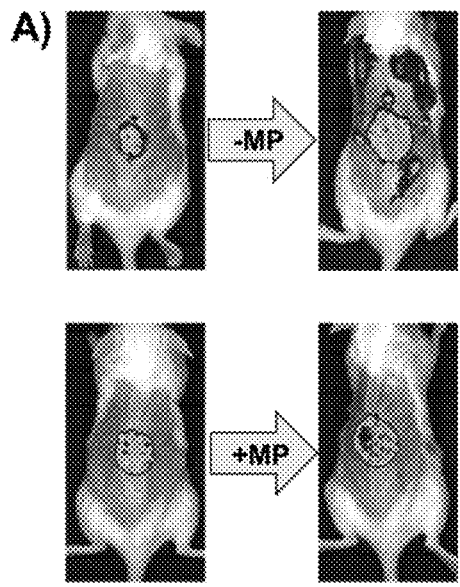
FIGS. 15A to 15C are graphs with imaging that show that antibiotics protect against dispersal-induced septicemia, and GH treatment augments antibiotic efficacy. Topical or systemic (pictured) meropenem (MP) protected against 10% α-amylase and cellulase (1:1; GH) dispersal-induced septicemia (FIG. 15A). Wounds were treated with heat-inactivated (HI) enzyme control, with or without concurrent topical MP (3 mg/ml) every 24 hours for 3 days, starting at hour zero. GH therapy significantly improved infection clearance vs. MP and HI enzyme (FIG. 15B). Luminescence quantification and representative IVIS® images of woundbeds on treatment day 3 showed complete clearance of enzyme plus antibiotic treated wounds (FIG. 15C). One-way ANOVA and the Tukey-Kramer multiple-comparison test were used to test for differences between column *$p<0.01$ ***$p<0.001$. N=9 for each group.
Figure 15B:
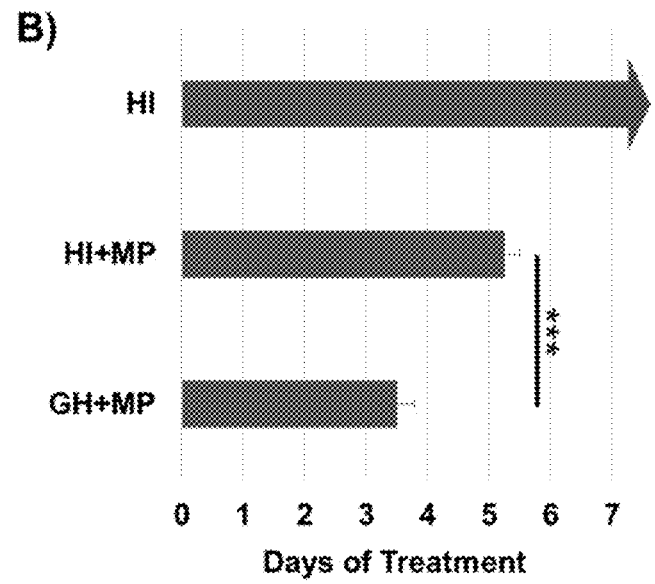
Figure 15C:
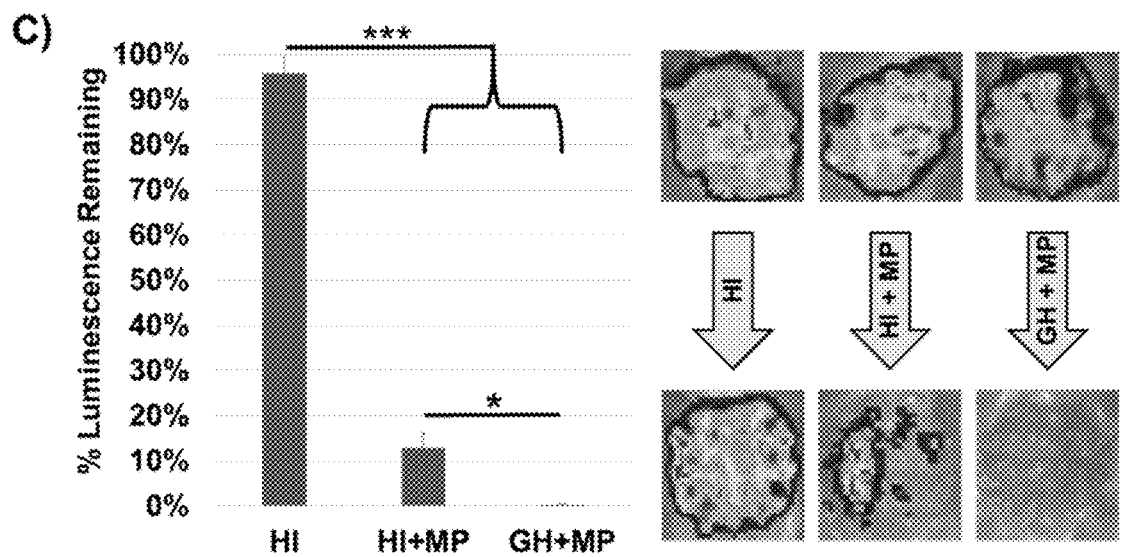

Antibiotics protect against dispersal-mediated septicemia, and are potentiated by concurrent GH therapy. To test if concurrent systemic or topical antibiotics can protect against dispersal-mediated septicemia, 48-hour chronic wound infections comprised of bioluminescent $P.$ $aeruginosa$ were treated with 10% GH as above, and monitored via IVIS for systemic spread. Both topical (3 mg/ml) and systemic (300 mg/kg) administration of meropenem prevented dissemination of $P.$ $aeruginosa$ (FIG. 15A). In addition to shielding the host from bacteremia, daily measurement of luminescence signal loss prior to daily treatments with heat-inactivated 10% GH alone, heat-inactivated GH plus topical meropenem (3 mg/ml), and 10% GH plus meropenem revealed that infection clearance occurred significantly faster for the GH plus meropenem group (FIGS. 15B-15C).

With a plethora of dispersal agents currently in development and pre-clinical testing, the question has been raised as to what effect triggering a large-scale, planktonic release of biofilm microbes will have on the patient [3, 6]. Christensen et al. showed that reducing cyclic-di-GMP levels in implant-associated $P.$ $aeruginosa$ biofilms via induction of phosphodiesterase activity caused a temporary but seemingly harmless accumulation of bacteria in the spleen [27]. However, potentially fatal systemic spread resulting from substantial biofilm dispersal has never been reported.

The dependence on swimming motility was determined by comparing mice infected with either wild-type *P. aeruginosa*, a flagellated Gram-negative chronic wound pathogen, with a flagellar knockout mutant, as well as with *S. aureus*, a non-motile wound pathogen, and treating each with 10% GH and monitoring for signs of a systemic infection. Only the animals harboring wild-type, motile *P. aeruginosa* developed fatal sepsis, indicating that swimming motility is important for dispersal-induced septicemia.

Wound size is also an important factor for the induction of dispersal-induced septicemia. When *P. aeruginosa*-infected mouse chronic wounds of varying sizes were treated with 10% GH, it was found that increasing the wound diameter, from 0.5 cm, to 1.0 cm, to 1.5 cm, correlated with increased bacteremia. This size-dependent response is not likely due to increased overall bacterial load, as no significant differences in microbial load were observed between the small and medium wounds, or between the medium and large wounds. Instead, the greater bloodstream accessibility that comes with increased wound surface area is the most probable factor. It should be noted that 1.0 cm- and 1.5 cm diameter wounds are roughly equivalent to 12.5% and 22% total body surface area (TBSA) respectively (based on Meeh's formula; TBSA in m2=9.83×[weight in kg×1 o000] 2/3/10000), or 18% based on the Wallace rule of nines [28], and a similar sized chronic wound is unlikely for the majority of human cases. Concerning diabetic foot ulcers, for example, the entire foot is less than 2% TBSA (rule of nines). Thus, dispersal-induced septicemia may be of less concern in real-world clinical cases.

Another factor to consider regarding the clinical-relevance of dispersal-induced septicemia is that patients with a chronic biofilm infection will most likely be on an antibiotic regimen [29, 30], and, as GH treatment of biofilms is a non-bactericidal approach [14], it would most-likely be implemented as an adjunctive therapy to normal antibiotic administration. Concurrent treatment with both systemic and topical meropenem protected mice from dispersal-mediated septicemia induced by 10% GH. Furthermore, 10% GH potentiated topical meropenem activity against wounds infected *P. aeruginosa*, and significantly decreased the time required to clear the infection vs. heat-inactivated enzyme control and meropenem alone. Thus, simultaneous GH plus antibiotic therapy represents a prospective new approach to managing chronic biofilm infections. Meropenem was chosen as a clinically-relevant, broad-spectrum antibiotic that does not contain either linkage targeted by the α-amylase and cellulase mixture. It should be noted that meropenem, like most antibiotics, targets only metabolically active cells, showing that the newly-dispersed cells are in fact metabolically active.

Example 3. Clinical Glycoside Hydrolase Application

Chronic infections often owe their recalcitrance to the presence of a biofilm, a community of microorganisms protected by a matrix of extracellular polymeric substance (EPS), that is comprised by a multitude of constituents, including polysaccharides, extracellular DNA (eDNA), proteins and lipids. Upwards of 80% of all human bacterial infections are biofilm-associated [2], and they are a life-threatening complication for a range of disease-states, such as cystic fibrosis, chronic obstructive pulmonary disease, diabetic foot ulcers, and implanted device infections [3].

Thus, biofilm infections are a pervasive and detrimental problem plaguing the healthcare field. Chronic foot ulcers alone directly add 9-13 billion dollars per year to the cost of diabetic care in the United States, and the total cost for all biofilm-associated infections in the United States was estimated at 94 billion dollars in 2010.

Due to the prevalence and recalcitrance of biofilm infections, which can offer the dwelling microorganisms up to a 1000% increase in tolerance to antimicrobials, researchers have begun investigating therapies that directly target the EPS, dispersing the microbes into their more vulnerable, planktonic state. As described hereinabove, the current state of research into medical biofilm dispersal, and utilizing glycoside hydrolase (GH) therapy to target structural EPS polysaccharides in order to break down chronic wound bacterial biofilms and disperse the resident microbes, potentiating antibiotic efficacy against them. It is shown herein that GH therapy was effective on both in vitro and in vivo biofilms, and that while large-scale dispersal was capable of releasing a dangerous, septicemia-inducing microbial load, this effect could be easily countered with conjunctive antibiotic treatment. Therefore, GHs represent promising adjunctive agents to existing medical biofilm infection therapies.

Bacterial strains. *P. aeruginosa* strain PAO1 [Holloway B W, Krishnapillai V, Morgan A F. Chromosomal genetics of *Pseudomonas*. Microbiol Rev. 1979; 43(1):73-102. Epub 1979/03/01] and *S. aureus* strain SA31 [Watters C, Everett J A, Haley C, Clinton A, Rumbaugh K P. Insulin treatment modulates the host immune system to enhance *Pseudomonas aeruginosa* wound biofilms. Infect Immun. 2014; 82(1): 92-100. Epub 2013/10/16] have been previously described. Fluorescently tagged *S. aureus* (Wheat Germ Agglutinate-TritC-stained) and *P. aeruginosa* (GFP insertion) were grown in baffled Erlenmeyer flasks, with shaking at 200 rpm, in Luria-Bertani (LB) broth at 37° C. Planktonically grown cells were then used to initiate infection in the in model at OD 0.004.

Glycoside hydrolases. Bacterial alpha-amylase (from *Bacillus subtilis*; MP Biomedicals, LLC #02100447) and fungal cellulase (from *Aspergillis niger*; MP Biomedicals, LLC #02150583) were utilized for these experiments. All enzymes were prepared by dissolving lyophilized powder in 1× phosphate-buffered saline (PBS) at 65° C. for 5 minutes. Heat-inactivated controls were generated by heating the enzyme solutions at 95° C. for 20 minutes.

Biofilm growth for Confocal Scanning Laser Microscopy. Biofilms were grown and observed in situ on a confocal microscope (Zeiss Imager.Z2 microscope with LSM 880 CLSM running Zeiss Zen 2010v. 6.0) for qualitative and quantitative analysis of z-stacks over a time series. To establish the biofilm, overnight cultures were grown in LB broth at 37° C. and inoculated into standard flow cells by the method of Tolker-Nielsen and Sternberg [Tolker-Nielsen T, Sternberg C. Growing and analyzing biofilms in flow chambers. Current protocols in microbiology. 2011; Chapter 1:Unit 1B.2. Epub 2011/05/04] with the modifications of Hutchison et al. [10]. The flow cell system was filled with preheated 3% TSB broth with 1% glucose, and each chamber was inoculated with 200 μL of bacterial culture. 1 hour of no-flow was then allowed in order for the bacteria to attach to the glass coverslip before flow was started. After 48 hours of growth under laminar flow at 3 ml h−1, the established biofilms were ready for treatment by adding GH or heat-inactivated GH (control) to the flow media.

Visualizing biofilm degradation and dispersal. In order to image biofilm degradation and dispersal, flow was temporarily ceased following biofilm growth (prior to GH treatment) by fluorescently labeled bacteria. Flow was then resumed and GH or vehicle control was added to the media as above for continuous visualization of bacterial dispersal via confocal microscopy.

Human debridements. Clinical samples were obtained courtesy of the Southwest Regional Wound Care Center. Surgical debridements were taken, and the relative microbial species abundance estimated via 16S PCR. Debridement samples were then divided into multiple pieces so that each could be subjected to multiple treatments (i.e. heat-inactivated control and enzyme treatments). Briefly, the sample sections were placed in 1 mL of enzyme or control solutions at 37° C. without agitation. Treatments proceeded for four hours, after which percent dispersal was determined by plating supernatant and the remaining, homogenized biofilm on non-selective (LB) agar, and finding the quotient of the total CFU (biofilm-associated plus planktonic) divided by the planktonic CFUs (in the supernatant).

The Increased EPS Complexity of Polymicrobial of Clinical Biofilms. Most of what is known about biofilm infections, and most of the pre-clinical research that has, and is, being done to combat them, is performed using in vitro models with a single microbial species. However, such studies fail to accurately represent the intricate nature of the in vivo infections the present inventors observed clinically, where there exists complex interplay between host and microbes, vastly different environmental conditions from patient to patient, and discrepancies between in vitro and in vivo biofilms in terms of structure, gene expression, size, nutrient availability, and many other factors. This is especially true when you consider that the majority of chronic infections, especially those that interface with the outside environment, such as chronic wounds, can be highly polymicrobial. For example, chronic wound infections have been estimated to contain, on average, more than five species per biofilm, with more than 30 species per wound having been detected in some instances. This adds multifarious inter-species interactions, as well as layers of structural and chemical complexity that aren't a factor for mono-species, or even limited-species biofilms. In addition, may microbial species have been shown to be biofilm contributors. In fact, one meta-analysis of 454 wound biofilms from diabetic patients found more than 1600 unique bacterial species involved in the infections [Citron D M, Goldstein E J, Merriam C V, Lipsky B A, Abramson M A. Bacteriology of moderate-to-severe diabetic foot infections and in vitro activity of antimicrobial agents. J Clin Microbiol. 2007; 45(9):2819-28. Epub 2007/07/05]. Thus, any biofilm eradication research must take clinical relevance into account by testing therapeutics on polymicrobial biofilms of in vivo origin.

Figure 16:
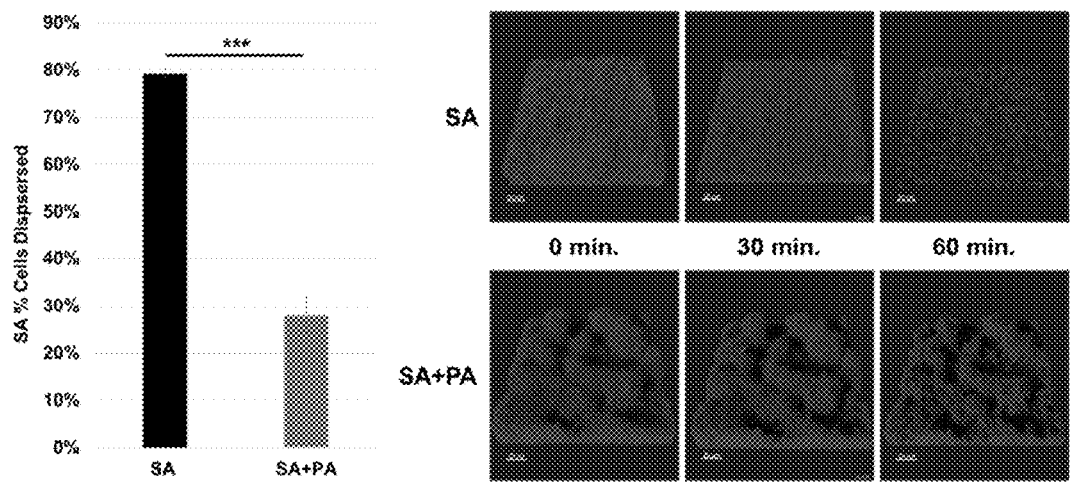
FIG. 16 is a graph with imaging that shows that glycoside hydrolase treatment is less effective against dual-species biofilms when compared to single-species. Treatment of 48-hour, *S. aureus* (SA) or *S. aureus* and *P. aeruginosa* (SA+PA) biofilms grown in flow cells with 5% glycoside hydrolase (1:1 α-amylase and cellulase) for 1.5 hours resulted in significantly less dispersal of *S. aureus* from the dual-species biofilms. Visual representations of SA and SA+PA biofilms 0, 30, and 60 minutes post-treatment are shown. One-way ANOVA and the Tukey-Kramer multiple-comparison test were used to test for differences between columns: ***$p<0.001$. N=4 for each group.

Efficacy loss correlates to degree of polymicrobicity. In order to test how increased microbial diversity within a biofilm affects the effectiveness of GH therapy in dispersing the cells, the inventors first compared the dispersal rates of single- and dual-species biofilms by quantifying bacterial loads before and after GH treatment within the flow-cell CSLM system. 48-hour biofilms consisting of S. aureus alone, or S. aureus and P. aeruginosa were established in individual flow cells and treated with 5% GH for 1.5 hours. When the dispersal rates of S. aureus between mono- and dual-species biofilms were compared, the inventors found that the bacteria were released from the single-species biofilms at a significantly higher rate (FIG. 16).

Figure 17:
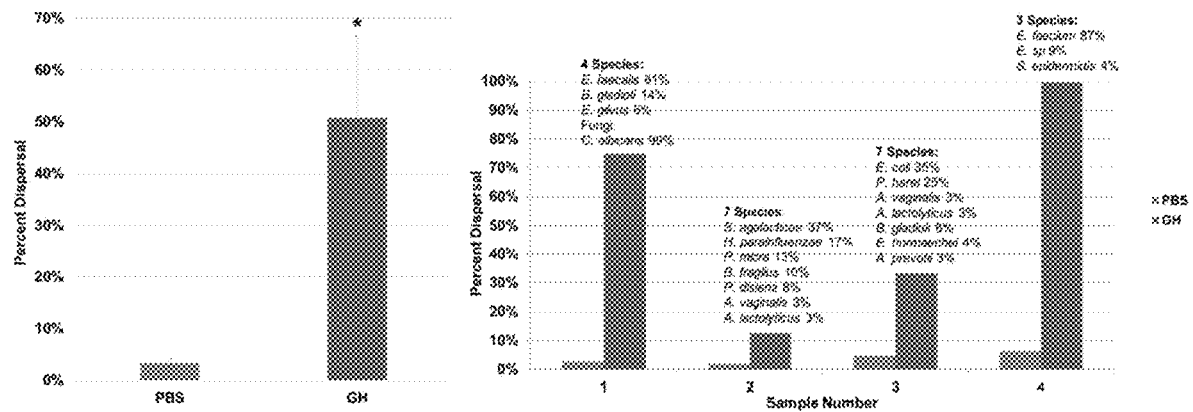
FIG. 17 are graphs that show that Glycoside hydrolase treatment is effective against human biofilm debridements, but efficacy is negatively correlated with degree of polymicrobicity. Treatment of human chronic wound biofilm debridements with 10% glycoside hydrolase (GH; 1:1 α-amylase and cellulase) or vehicle control (PBS) for 4 hours resulted in significant mean dispersal across all samples (A). However, dispersal was negatively correlated ($p=0.0247$; Pearson r) with the number of species present in each sample (B). One-way ANOVA and the Tukey-Kramer multiple-comparison test were used to test for differences between columns.*$p<0.05$.

This shows that the added complexity of the two-species biofilm impedes GH activity against it. When considering clinical biofilms, they can be even more complex and polymicrobial, with some chronic wounds having been shown to harbor more than 30 different microbial species at once [Wolcott R D, Hanson J D, Rees E J, Koenig L D, Phillips C D, Wolcott R A, et al. Analysis of the chronic wound microbiota of 2,963 patients by 16S rDNA pyrosequencing. Wound Repair Regen. 2015. Epub 2015/10/16]. This level of structural and compositional intricacy is something that the inventors are incapable of modeling in vitro, and it is similarly unlikely that such species diversity could be established and maintained in this in vivo mouse chronic wound model. Therefore, in order to examine the effects of increased polymicrobicity on GH therapy, the inventors obtained clinical chronic wound biofilm samples and tested the efficacy of GH against each in comparison to vehicle controls. The inventors found that, on average, GH therapy was effective against the range of samples, but that the more species involved in the biofilm infection, the less dispersal was observed for the sample (FIG. 17). PCR-determined data can be used to more accurately quantify species-specific dispersal from the biofilms, especially for the difficult-to-culture, obligate anaerobic and slow-growing, fastidious organisms.

Figure 18:
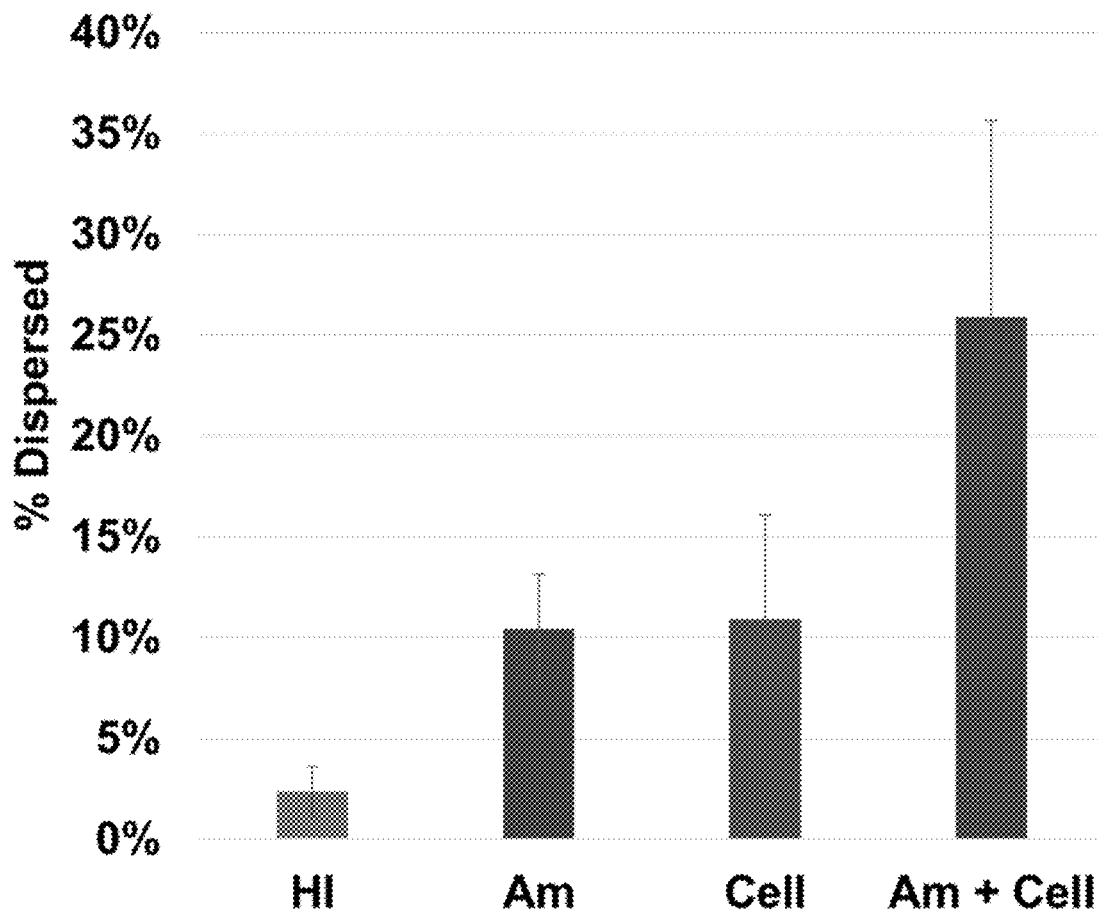
FIG. 18 is a graph that shows that dual-enzyme treatments are more effective than single enzymes against human chronic wound biofilm debridement samples. Treatment of human chronic wound biofilm debridements with 10% glycoside hydrolase (α-amylase (Am), cellulase (Cell), or both (Am+Cell) for 4 hours resulted in greater average dispersal for the dual-enzyme therapy in comparison to single-enzymes, and heat inactivated dual-enzyme (HI) control.

This implies that the more polymicrobial a biofilm, the more chimeric the mixture of its structural components, and the less likely that targeting a particular glycosidic linkage will lead to significant degradation of the EPS matrix. To test this further, the inventors compared the activity of α-amylase, cellulase, and the two enzymes in combination against human chronic wound biofilm debridement samples with varying degrees of polymicrobicity, and found that for most samples, the dual-enzyme combination was more effective than either enzyme alone (FIG. 18).

Therefore, the most practical way forward for increasing efficacy against clinical infections is to utilize a multifaceted combination of enzymes, including not only GHs that target a wide range of linkages, but also enzymes that degrade other important matrix components, such as proteases and DNAses.

Potential for Collateral Damage to the Host. All therapeutics must take into account potential collateral damage to the host. This is especially true for multifaceted, broad-spectrum compounds with highly conserved, cross-kingdom targets. Existing antibiotics and other antimicrobials owe their safety to the physiological difference between prokaryotes and eukaryotes, and likewise between fungal and animal cells. For example, common antibiotic targets are the unique, bacterial protein, cell wall, and DNA or RNA synthesis machinery. However, targeting extracellular EPS structural elements raises the likelihood that unintentional local or systemic damage to the host will occur. For instance, while exoproteins are an important structural component for many biofilm-producing microorganisms, the proteases that degrade them, such as trypsin or proteinase K, may also damage important host proteins. Conversely, DNAses are unlikely to cause damage to the host, given that they are not transported into cells, and instead degrade extracellular DNA exclusively. As shown herein, any EPS-targeted treatment must be implemented with the composition of the infection site, as well as any possible systemic interactions, kept in mind.

Glycoside hydrolases and host linkages. While glycosidic linkages are present in humans they are not readily found in human tissue, and thus GHs are unlikely to pose significant risk when used topically. In fact, both α-amylase and cellulase are FDA-approved food additives, have been used in food processing for years, and have been found to be safe for human consumption. However, for other EPS targets, such as proteins and lipids, they are more likely to be encountered in the host, giving the enzymes that degrade them a greater potential for causing collateral damage.

The Potential for Resistances to Develop. Bacteria are highly adept evolvers. Due to both their rapid generation time, and their common propensity for mutation, bacterial populations are genetically diverse. Therefore, any bactericidal agent has the potential to leave a resistant sub-population unharmed and able to re-establish their numbers. Antibiotic resistance, for example, is a major problem facing the healthcare field today, largely due to the overzealous use of antibiotics in both the clinical and agricultural settings. Any new therapeutic, especially those that will be widely used in a broad-spectrum manner, has the potential to be rendered ineffective due to the selection of resistance mechanisms in microbial populations. That being said, EPS-targeted agents such as GHs, which have little to no effect on the microbes themselves are unlikely to see resistance develop against them. That is, since GHs are non-bactericidal, no selection inherently takes place. Instead, as an augmentative agent to existing antimicrobials, GHs have the potential to potentiate existing drugs to the point where they can subvert biofilm-bolstered MICs by killing the newly-liberated, more-susceptible planktonic bacteria. For multi-faceted, matrix-degrading enzyme cocktails, even if resistances were to develop over time, it may very well be an adaptation away from the biofilm mode of life, which could prove medically beneficial in its own right.

These concerns aside, utilizing ex vivo treatment of human chronic wound biofilm debridements, the present inventors were able to demonstrate that GH efficacy negatively correlates with the number of species involved in the infections. The inventors hypothesize that the addition of GHs, along with other enzymes that target conserved EPS structural components, can increase the broad-spectrum efficacy of the dispersal agent "cocktail." However, any potential collateral damage to the host must be accounted for when considering the enzymatic targets of each agent, especially those targets that are highly present in the host ECM, such as proteins. The potential development of resistance to the dispersal agents must also be accounted for in long-term, recalcitrant infections. The therapeutics least likely to cause selection are those that are not inherently antimicrobial, but instead act merely as an adjunctive to existing therapeutics and immune cells. Lastly, since these dispersal agents are foreign to the host, there will likely be an antibody response generated against them over repeated administrations during the course of highly chronic infections. Any effects that this antibody response will have on enzymatic activity, as well as on the host itself, should be investigated.

Thus, the present inventors have demonstrated the noteworthy ability of GH therapy to break up biofilms and augment antimicrobial action in both in vivo animal models and ex vivo clinical samples.

Example 4. Glycoside Hydrolases as Biofilm Dispersal Agents

For the majority of time since the discovery of microorganisms, bacteria were thought to exist as community-independent, free-floating planktonic cells. Today, largely thanks to the work started by John William Costerton, it is known that bacteria often reside in vast communities of aggregates protected by a self-synthesized extracellular polymeric substance (EPS) that can confer up to 1000% increased tolerance to antimicrobials, as well as protection against the host immune system. Biofilms are found ubiquitously in natural and manmade environments (plumbing fixtures, food processing surfaces, marine vessels, etc.), providing protection against environmental stressors such as desiccation and foraging by predators, and are highly associated with chronic infections in the clinical setting. In fact, bacterial biofilms are implicated in around 80% of all non-acute human bacterial infections, including more than 90% of all chronic wound infections. The added protection of the biofilm mode of life has only served to exacerbate the rapidly increasing development of antibiotic resistance, and all too often biofilm-associated infections prove too recalcitrant to eradicate, leading to the morbidity and/or mortality of the patient. In the United States, diabetics suffering from non-healing foot ulcers alone directly cost 9-13 billion dollars per year to manage, and diabetics are 8 times more likely to require a lower limb amputation than non-diabetics.

Biofilm dispersal as an augmentative therapy. Traditionally, fighting infection involved actively targeting the causative pathogen via antimicrobial agents. However, living within the protection of a biofilm effectively reduces the concentration of antimicrobial agent that each individual pathogen encounters, and the antibiotic concentration required to eradicate biofilm-dwelling bacteria is often higher than that which is practically achievable in vivo if administered systemically [Bjarnsholt T, Ciofu O, Molin S, Givskov M, Hoiby N. Applying insights from biofilm biology to drug development—can a new approach be developed? Nat Rev Drug Discov. 2013; 12(10):791-808. Epub 2013/10/02]. Therefore, treatments that can effectively degrade the EPS in a non-microbicidal way can serve as adjunctive therapies to potentiate antimicrobial activity against the dispersed, planktonic microbes. In this way, the effectiveness of existing therapies can be increased, in addition to potentially revitalize older drugs that have long-since been rendered ineffective at safe doses against biofilm-associated infections.

There are many strategies to achieve biofilm dispersal, including, but not limited to: inhibition of EPS synthesis and secretion systems, the use of EPS adhesin- or structural component-binding antibodies (passive vaccination) or inhibitors, up- or down-regulation of endogenous pathways involved in biofilm synthesis and dispersal (i.e. the cyclic-di-GMP pathway), quorum-sensing inhibition, and active enzymatic degradation of integral EPS matrix structural constituents such as proteins, eDNA, and exopolysaccharides [Koo H, Allan R N, Howlin R P, Stoodley P, Hall-Stoodley L. Targeting microbial biofilms: current and prospective therapeutic strategies. Nat Rev Microbiol. 2017; 15(12):740-55. Epub 2017/09/26]. Each strategy carries with it the potential to weaken established biofilms, making the associated microbes more-susceptible to antimicrobial agents and the host immune system, and to inhibit biofilm recurrence. It is important to note the most multifaceted treatments comprised of a spectrum of dispersal agents with separate targets carry the most potential as an effective, practical, clinical therapeutic. This is especially true for complex, polymicrobial infections, like those seen in chronic wounds, which can harbor more than 30 microbial species at once [Wolcott R D, Hanson J D, Rees E J, Koenig L D, Phillips C D, Wolcott R A, et al. Analysis of the chronic wound microbiota of 2,963 patients by 16S rDNA pyrosequencing. Wound Repair Regen. 2015. Epub 2015/10/16]. Such infections contain a chimeric mixture of EPS components contributed to by the variety of microbial species present, and as such, significant degradation would most likely be achieved by a broad-spectrum, multi-threat dispersal agent solution.

Targeting exopolysaccharides. Exopolysaccharides are the major EPS component for many species of pathogen. In fact, before it was understood that the biofilm matrix contained a plethora of different constituents, the original descriptor for the acronym, EPS, was not "extracellular polymeric substance," but "extracellular polysaccharide." Not only are they major EPS structural components, but they are also involved in numerous other processes vital to the initiation and persistence of biofilms, including but not limited to: surface and scaffolding adhesion, microbial aggregation, desiccation tolerance, nutrient sorption and storage, enzyme binding, and physical protection against antimicrobials and host defenses. Due to their immense utility for the initiation, maintenance, and integrity of biofilms, it is no wonder that exopolysaccharides are a common target for prospective dispersal agents.

The present inventors also investigated the effects of two common glycoside hydrolases (GHs), alpha-amylase and cellulase, in the treatment of biofilm infections, specifically chronic wound bacterial biofilm infections. Currently, the polysaccharide composition of multiple, prevalent, biofilm-producing bacterial pathogens has been elucidated, and the ideal GH dispersal agent would act on highly conserved glycosidic linkages as to achieve broad-spectrum efficacy against the polysaccharides produced by a range of pathogens. One glycosidic linkage that is especially conserved among EPS exopolysaccharides is the β-1,4 bond, such as that present in cellulose, which is common to certain strains of *E. coli, Salmonella, Citrobacter, Enterobacter, Pseudomonas*, and more. Cellulase is a commercially available enzyme that hydrolyzes these β-1,4 linkages, and thus could serve to break up a host of biofilm exopolysaccharides into simple sugars, triggering structural collapse of the EPS matrix. Another common EPS glycosidic linkage is the α-1,4 bond, and α-amylase, a GH that acts by cleaving the bond, has been previously shown to inhibit the biofilm formation of, as well as disrupt the pre-formed biofilms of, *Vibrio cholerae, Staphylococcus aureus* and *Pseudomonas aeruginosa*, in vitro.

Alpha-amylase and cellulase are prime enzymes for a broad-spectrum clinical dispersal therapy, not only because of the ubiquity of the targeted bonds, but also because of their availability and cost-effectiveness. Both enzymes are commercially mass-produced for food and textile processing, are FDA-approved food additives, and have been found to be safe for human consumption. Additionally, cellulase is already used medicinally for the treatment of "bezoars" (indigestible masses of material in the GI tract) with no ill effects reported, providing a safety and efficacy precedent. For both enzymes, the present inventors hypothesize that, due to the inherent lack of the target glycosidic linkages within the tissue of the wound-bed periphery, host-tissue toxicity will be negligible. Since experimental drug-toxicity more typically arises from systemic exposure, the topical application of GHs should pose a minimal risk, it is not expected to have significant infiltration into the blood stream. The results herein show no host toxicity when using the enzymes on murine tissue. To investigate the host toxicity of GH solutions, various tissue samples, including dermis, adipose, muscle, and connective tissue, can be collected from the wound-bed peripheries of chronically wounded (uninfected) mice. The tissue would then be submerged in solutions of increasing concentrations of enzymes for 24 hours and monitored for signs of degradation (increases in elasticity, disintegration, discoloration, etc.) in comparison to control tissue submerged in saline. Mice could be given uninfected chronic wounds, into which increasing concentrations of GH would be injected. The mice would be monitored for a period of 48 hours for symptoms of toxicity, including dermatitis and inflammation, as well as more severe effects, such as skin and organ damage (observed during autopsy). The highest effective dose, which does not cause toxic damage, would be utilized.

Glycoside hydrolases for the treatment of biofilm infections. The present inventors also demonstrated the potential of glycoside hydrolases as an augmentative treatment for biofilm infections. Utilizing enzymes that target highly conserved linkages in structural EPS polysaccharides, the inventors were able to achieve significant biofilm degradation in a clinically relevant in vitro model, as well as in ex vivo and in vivo treatment of murine chronic wound biofilms. Additionally, it is shown that GH efficacy is negatively correlated with polymicrobicity in human chronic wound biofilm debridement samples, and that the dual-enzyme treatment was more effective than single enzymes. This shows that additional enzymes with different matrix targets, including other exopolysaccharide glycosidic linkages, eDNA, and structural exoproteins, could be added to increase the broad-spectrum potential of the therapy, especially against the more complex infections containing a variety of pathogen species, contributing a chimeric mixture of EPS matrix constituents. The observed biofilm degradation correlated to significant cell dispersal in all tested models, with no associated antimicrobial activity. This is important, because any antimicrobial agent will create a selective pressure for the development of resistant subpopulations. By targeting excreted microbial products without actively killing the cells, the risk of resistance is minimized. Lastly, the inventors found that the dispersed cells were less tolerant to antibiotic killing, and that GH treatment significantly reduced the time required for antibiotic treatment to clear a chronic wound biofilm infection. This shows that, as a potential clinical therapy, GH therapy could be a very effective adjunctive that would potentiate existing treatments against biofilm infections.

Versatility of glycoside hydrolase therapy. Although the results of this particular project deal heavily with chronic wound biofilm infections, it is important to note that GH therapy carries potential applicability to a variety of infection types. In fact, due to the nature of chronic wounds, with factors such as host immunoincompetence, easy access by environmental pathogens, and their persistence within a nutrient-rich site, chronic wounds are particularly prone to complex, polymicrobial infections that make broad-spectrum EPS-targeted treatments less-likely to be successful. Other infection types, such as chronic otitis media, conjunctivitis, sinusitis and cystic fibrosis lung infections, which are less prone to harboring multiple species of pathogens at once, would theoretically be more-susceptible to GH-mediated degradation. It should be noted that certain biofilm-associated infections, such as foreign-body infections (i.e. prosthetic joints and artificial heart valves), osteomyelitis, and endocarditis, would be less likely to be treatable by GH therapy, given the impracticality of topical administration to the sites.

Biodelivery. As mentioned hereinabove, many experimental antibiofilm agents are in pre-clinical development. However, in vitro efficacy often fails to be replicated in vivo. Furthermore, while some agents prove to be effective at prophylaxis, they often fall short at treating mature, established wound infections, greatly reducing their clinical applicability. Much of this impotence is due to inadequate biodelivery, whereby the drug is inactivated, sequestered or otherwise cleared from the wound, or fails to penetrate into the lower layers of the dermis where biofilms persist. The present invention achieved biofilm degradation and dispersal in vivo. To enhance biodelivery, more efficient vehicles, such as hydrogels or drug-loaded bandages, can be used to enhance GH activity. As shown herein, various methods can be used to administer the enzymes in a controlled manner in vivo over a longer course of time to give the host immune system a chance to mount a prolonged and powerful attack against the dispersed cells, reducing the risk of dispersal-induced septicemia.

Effects of Large-Scale Biofilm Dispersal on the Host. During the course of this project, the inventor made a surprising discovery that is applicable, and crucial to, the entire field of medical biofilm dispersal. It had previously been theorized that a massive dispersal event, if it could be triggered in a living animal, may potentially overwhelm the immune system and lead to septicemia [9]. Surprisingly, the present inventors found that in vivo GH therapy of mouse chronic wound bacterial biofilm infections led to the eventual death of the majority of mice due to dispersal-induced bacteremia. In characterizing this fatal spread of bacteria, it was discovered that dissemination of *P. aeruginosa* occurred via the blood-stream. Also, the inventors showed that the induction of septicemia was dependent upon bacterial swimming motility, with a flagellar knockout mutant of *P. aeruginosa*, as well as the non-motile chronic wound pathogen, *S. aureus*, failing to disseminate. Additionally, wound-size is also important to the likelihood of dispersal-induced septicemia.

When the inventors infected wounds of differing sizes with similar bacterial loads, there was a positive correlation between wound diameter and septicemia, indicating that greater surface area provides increased access to the vasculature. Since the experimental wounds are significantly larger in proportion to the host than the vast majority of clinical chronic wounds, it stands to reason that dispersal-induced septicemia would be far less likely in clinical practice than in the animal model. In fact, when the inventors treated the smallest, most clinically relevant sized wounds with GH, no septicemia was observed in any of the animals. Nevertheless, it is possible give antibiotics in conjunction with GH treatment as a precaution, especially in immunocompromised patients. It is shown herein that topical and systemic antibiotics not only offered complete protection against GH dispersal-induced septicemia, but that GH augmented antibiotic efficacy, and decreased infection clearance times as well.

Example 5. Wound Healing Dressings and Compositions

A woven nylon bandage (e.g., Tegaderm) can be used for the dressing substrate. Tegaderm is commonly used in medical practice as a contact layer on top of wounds in surgical applications. The structure of the material is highly uniform, consisting of woven fibers of approximately 70 μm in diameter that form pores within the weave of nearly 0.01 mm². Coating the Tegaderm substrate with LbL film does not disturb these features, as was observed in scanning electron microscopy (FIGS. 20A to 20C).

Figure 19:
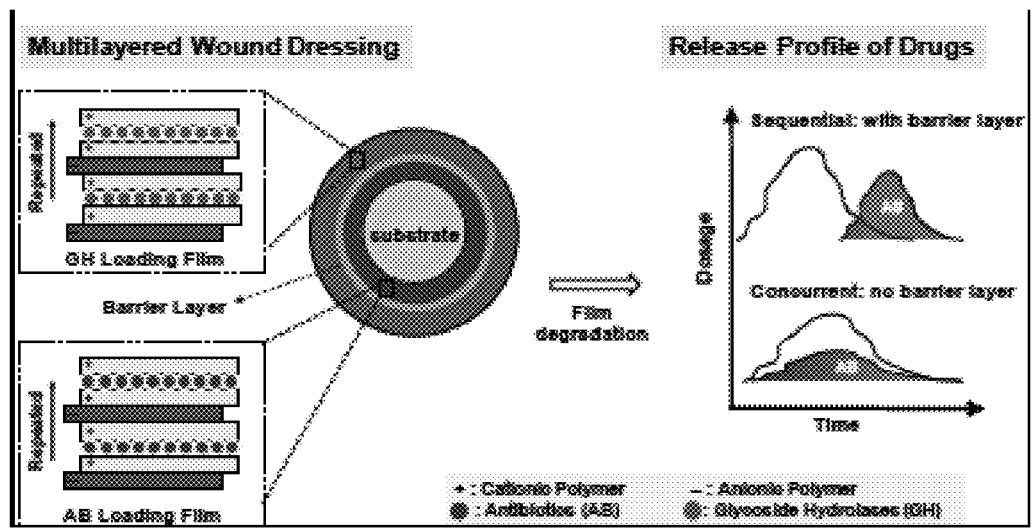
FIG. 19 shows a schematic illustration of the top down degradation of a multilayered film that allows for designed release profiles of GH and antibiotic (AB). The therapeutics can serve as primary nanolayer constituent of the film. Sequential or concurrent release of drug combinations can be precisely modulated by the selection of film composition and barrier layer for diffusion. Loading of drugs can be controlled by the numbers of repeating layers shown in the inset boxes. Substrate depicts the cross-section of a fiber in a wound dressing.

FIG. 19 shows a schematic illustration of the top down degradation of a multilayered film that allows for designed release profiles of GH and antibiotic (AB). The therapeutics can serve as primary nanolayer constituent of the film. Sequential or concurrent release of drug combinations can be precisely modulated by the selection of film composition and barrier layer for diffusion. Loading of drugs can be controlled by the numbers of repeating layers shown in the inset boxes. Substrate depicts the cross-section of a fiber in a wound dressing.

Figure 20A:
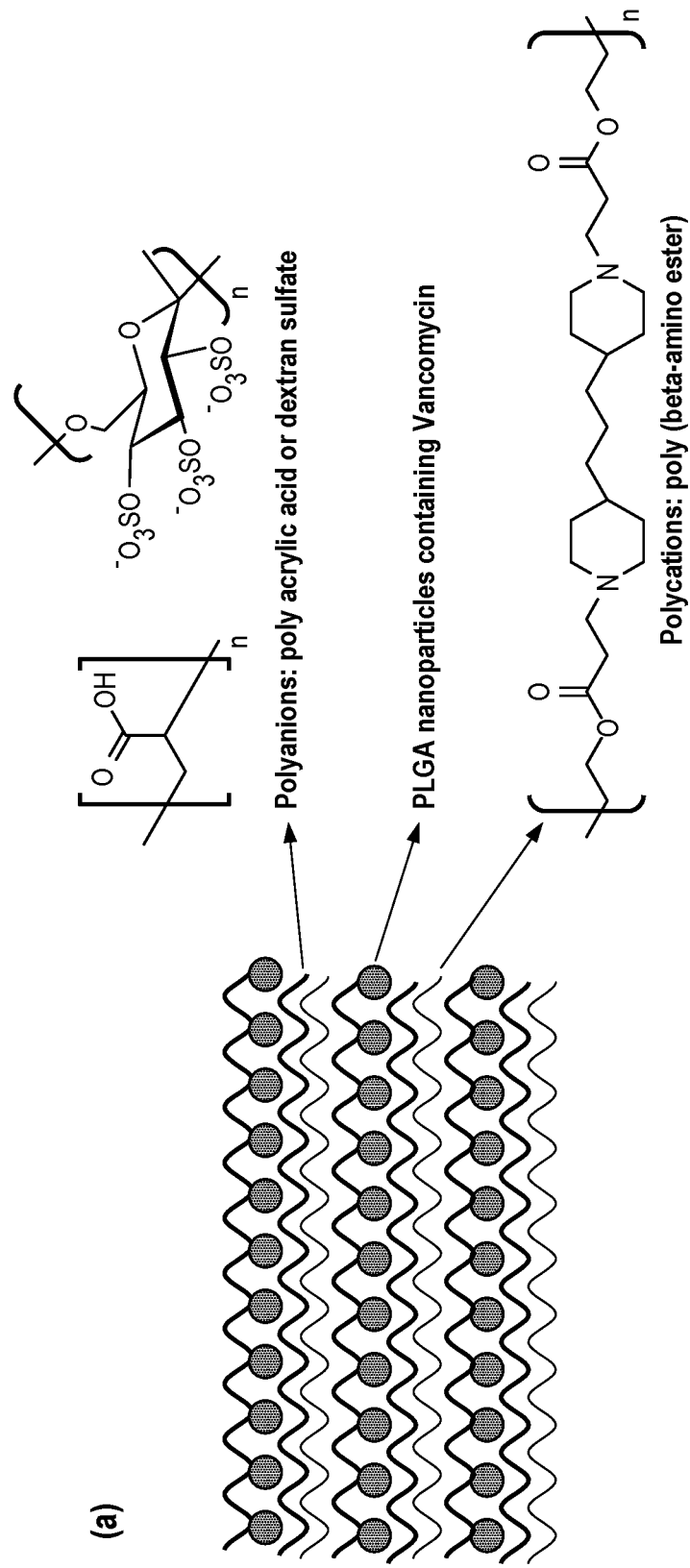
FIGS. 20A to 20C show.
Figure 20B:
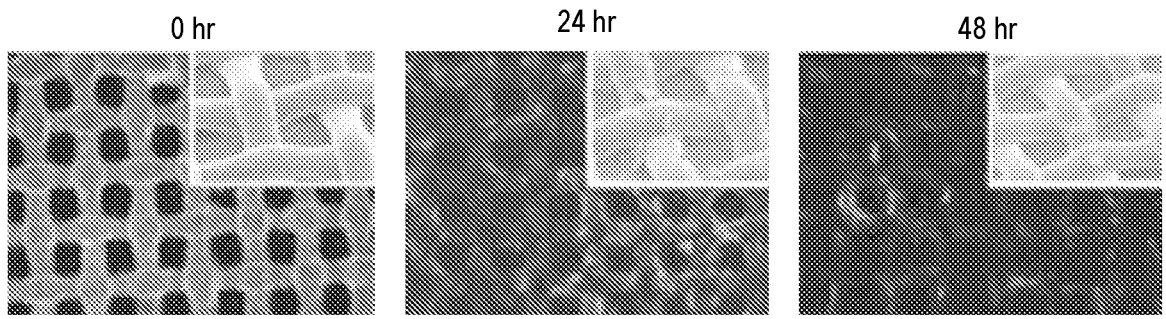
Figure 20C:
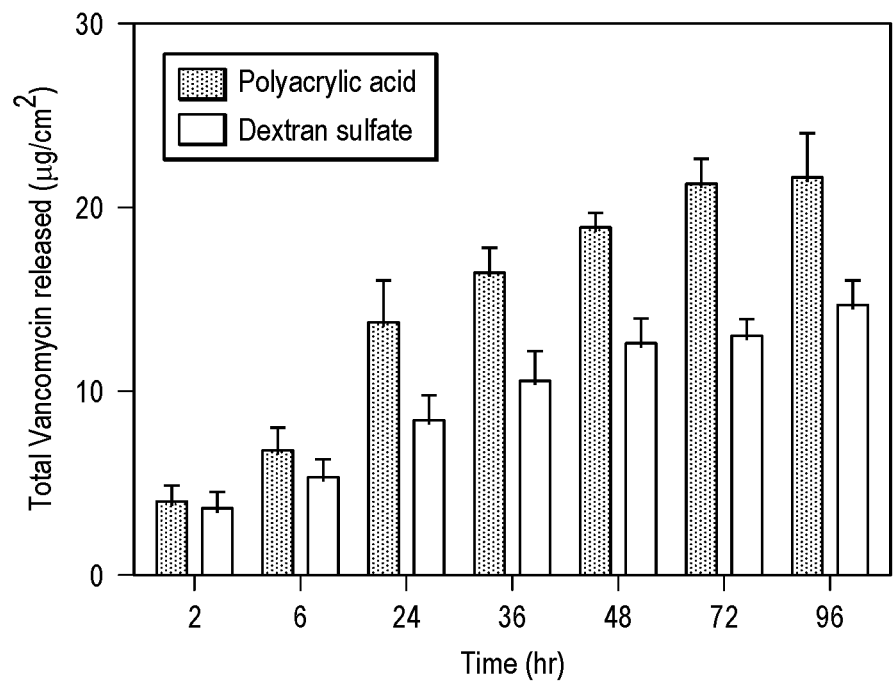

FIGS. 20A to 20C show: (FIG. 20A) Schematic illustration of the composition and structure of a multilayered film for releasing of Vancomycin. (FIG. 20B) Vancomycin loaded multilayered film (polyacrylic acid/PBAE/Vancomycin, 20 layers) was coated onto a wound dressing (Tegaderm). The film can be degraded by hydrolyzation, as shown in SEM and florescent images. Polyacrylic acid was labeled with FITC. Scale bar is 100 μm. (FIG. 20C) Release profile of Vancomycin can be adjusted by changing the film composition.

TABLE 3

Commercially available Glycoside hydrolases for use with the present invention.

| Enzyme | Bond(s) Hydrolyzed | Commercial Source | Natural Source |
|---|---|---|---|
| α-Amylase | α-1,4 | MP Biomedicals | *Bacillus subtilis* |
| Diastase | α-1,4 | Sigma | *Aspergillus oryzae* |
| Pectolyase | α-1,4 | Sigma | *Aspergillus japonicus* |
| Pectinase | α-1,4 | Sigma | *Aspergillus niger* |
| Invertase | α-1,4 | Sigma | *Saccharomyces cerevisiae* |
| Amylogulcosidase | α-1,4 (α-1,6, lesser) | Sigma | *Rhizopus* sp. |
| Dextranase | α-1,6 | Sigma | *Penicillium* sp. |
| Cellulase | β-1,4 | MP Biomedicals | *Aspergillus niger* |
| Xylanase | β-1,4 | Sigma | *Thermomyces lanuginosus* |
| Alginate lyase | β-1,4 | Sigma | Various algae |
| Cytohelicase | β-1,3 | Sigma | *Helix pomatia* |
| Inulinase | β-1,2 | Sigma | *Aspergillus niger* |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method for reducing biofilm present on a surface of an animal or a subject, wherein the method comprises:
    contacting the biofilm with a multilayered dressing, wherein a first layer comprises glycoside hydrolases that target α-1,4, β-1,4, and β-1,3 glycosidic linkages released first, followed by release of an antibiotic, wherein the antibiotic kills pathogenic bacteria after release from a biofilm and the antibiotic activity of the antibiotic is increased in the presence of the glycoside hydrolases, wherein the sequential release of the glycoside hydrolases followed by the antibiotic reduces dispersal of the pathogenic bacteria from the biofilm,
    wherein the biofilm is a biofilm-related infection that is on or at a wound, burn infection, keratitis, on a catheter, on a bioprosthetic, an indwelling medical device, a lung, a chronic pulmonary disease, or a lung infection of the animal or subject, and
    wherein the biofilm-related infection is caused by pathogenic bacteria selected from[,] *P. aeruginosa, S. aureus, E. coli, Aeromonas* spp., *Enterobacteriaceae* spp., *Candida* spp., *Aspergillus* spp., *Acinetobacter* spp., *T. asahii, B. cineria,* or *Fusarium* spp, and the biofilm that is a Pel-dependent, a Psl-dependent, a PNAG-dependent, or a GAG-dependent biofilm.

2. The method of claim 1, wherein the glycoside hydrolases are a bacterial alpha-amylase and a fungal cellulase, or are a bacterial alpha-amylase and a fungal cellulase at a 1:2, 1:1, or 2:1 ratio, or both.

3. The method of claim 1, wherein the glycoside hydrolases are at least 1, 2, 3, 4, 5, 7, 10, 12, 15, 20, 25, 30, 35, 40, 45, 50, 60, 70, 80, or 90% weight to weight of the multilayered dressing.

4. The method of claim 1, wherein the surface is on an animal or a subject and the method further comprising co-administering topically, systemically, or both an antimicrobial agent to the animal or the subject in need thereof.

5. The method of claim 1, wherein the glycoside hydrolases increase the effectiveness of the antibiotic at least 10, 20, 25, 30, 35, 40, 45, 50, 75, 100, 200, 300, 400, 500, 600, 700, 800, 900, or 1000%, when compared to a biofilm that is not exposed to the glycoside hydrolases.

6. The method of claim 4, wherein the subject that is treated is selected from the group consisting of human immunodeficiency virus (HIV) infection, sepsis, septic shock, acquired immunodeficiency syndrome (AIDS), leukemia, a lymphoma, rheumatoid arthritis, diabetes mellitus type I, Crohn's disease, chronic obstructive pulmonary disease (COPD), bronchitis, cystic fibrosis, emphysema, lung carcinoma, asthma, pneumonia and sinusitis, a subject preparing for, undergoing, or recovering from chemotherapy, radiotherapy, an organ transplant, a resident in a healthcare institution, a smoker, having a pre-established infection, an immunocompromised subject, a subject also undergoing intensive or critical care, a subject also suffering from trauma, a subject also suffering from a burn, a subject also suffering from an acute and/or chronic wound, a neonatal subject, an elderly subject, a subject also suffering from a malignant neoplasm, a subject also suffering from a non-malignant neoplasm, a subject also suffering from an auto-immune condition, a subject also suffering from reduced or abrogated epithelial or endothelial secretion and/or secretion clearance and a subject also fitted with a medical device.

7. The method of claim 4, wherein the method is for treating dental plaque, gingivitis, periodontitis, native valve endocarditis, acute otitis media, chronic bacterial prostatitis, pneumonia, asthma or device-related infection resulting from implantable and/or prosthetic medical devices or tissue replacements.

8. The method of claim 4, wherein the biofilm is in or on an internal or external body surface or interface selected from the group consisting of exposed skin, a surface in an oral cavity, a reproductive tract, a urinary tract, a respiratory tract, a gastrointestinal tract, a peritoneum, a middle ear or a prostate, vascular intima, conjunctiva, corneal tissue, lung tissue, heart valves, skin, scalp, nails, teeth, an interior of a wound, and an internal surface of a mammal.

* * * * *